(12) United States Patent
Rosi et al.

(10) Patent No.: US 11,491,231 B2
(45) Date of Patent: Nov. 8, 2022

(54) PEPTIDE-OLIGONUCLEOTIDE CHIMERAS (POCS) AS PROGRAMMABLE BIOMOLECULAR CONSTRUCTS FOR THE ASSEMBLY OF MORPHOLOGICALLY-TUNABLE SOFT MATERIALS

(71) Applicants: University of Pittsburgh-Of the Commonwealth System of Higher Education, Pittsburgh, PA (US); Northwestern University, Evanston, IL (US)

(72) Inventors: Nathaniel L. Rosi, Pittsburgh, PA (US); Andrea David Merg, Pittsburgh, PA (US); Ryan Vachon Thaner, Pittsburgh, PA (US); SonBinh T. Nguyen, Evanston, IL (US)

(73) Assignees: University of Pittsburgh—Of the Commonwealth System of Higher Education, Pittsburgh, PA (US); Northwestern University, Evanston, IL (US)

( * ) Notice: Subject to any disclaimer, the term of this patent is extended or adjusted under 35 U.S.C. 154(b) by 384 days.

(21) Appl. No.: 15/941,626

(22) Filed: Mar. 30, 2018

(65) Prior Publication Data
US 2018/0296682 A1 Oct. 18, 2018

Related U.S. Application Data

(60) Provisional application No. 62/480,176, filed on Mar. 31, 2017.

(51) Int. Cl.
*A61K 47/54* (2017.01)
*A61K 47/69* (2017.01)
*A61K 38/10* (2006.01)

(52) U.S. Cl.
CPC ............ *A61K 47/549* (2017.08); *A61K 38/10* (2013.01); *A61K 47/545* (2017.08); *A61K 47/555* (2017.08); *A61K 47/6921* (2017.08); *A61K 47/6923* (2017.08)

(58) Field of Classification Search
CPC ......................... A61K 47/549; A61K 47/6921
See application file for complete search history.

(56) References Cited

U.S. PATENT DOCUMENTS

| 8,999,947 | B2 | 4/2015 | Mirkin et al. | |
|---|---|---|---|---|
| 9,206,233 | B2 * | 12/2015 | Rosi | C07K 7/08 |
| 2001/0008771 | A1 * | 7/2001 | Seibel | A61K 47/62 |
| | | | | 435/455 |
| 2004/0034191 | A1 * | 2/2004 | Manoharan | C07K 9/00 |
| | | | | 530/322 |
| 2005/0106598 | A1 * | 5/2005 | Manoharan | C12N 15/113 |
| | | | | 435/6.14 |
| 2006/0172282 | A1 * | 8/2006 | Naik | C12N 15/1037 |
| | | | | 435/5 |
| 2008/0176760 | A1 * | 7/2008 | Naik | B82Y 30/00 |
| | | | | 506/9 |
| 2008/0221303 | A1 * | 9/2008 | Katzhendler | C07K 1/068 |
| | | | | 530/323 |
| 2009/0100969 | A1 * | 4/2009 | Rosi | B82Y 30/00 |
| | | | | 75/746 |
| 2012/0190124 | A1 * | 7/2012 | Smith | A61P 31/10 |
| | | | | 530/413 |
| 2012/0289457 | A1 * | 11/2012 | Hanson | A61P 31/16 |
| | | | | 514/3.1 |
| 2016/0304648 | A1 * | 10/2016 | Nadal | C09K 11/565 |
| 2017/0232109 | A1 * | 8/2017 | Mirkin | A61K 38/44 |
| | | | | 424/9.1 |

FOREIGN PATENT DOCUMENTS

WO WO 2016/028940 * 2/2016 ............. A61K 47/48

OTHER PUBLICATIONS

Abraham et al., "Controlled aggregation of peptide-DNA hybrids into amyloid-like fibrils," *Eur. Polym. J.*, vol. 65, pp. 268-275 (2015).
Andersen et al., "DNA Origami Design of Dolphin-Shaped Structures with Flexible Tails," *ACS Nano*, 2:1213-1218 (2008).
Bahar, et al., "Antimicrobial Peptides," *Pharmaceutical*, vol. 6, pp. 1543-1575 (2013).
Bennet, et al., "RNA Targeting Therapeutics: Molecular Mechanisms of Antisense Oligonucleotides as a Therapeutic Platform," *Annual Review of Pharmacology and Toxicology*, vol. 50, pp. 259-293 (Feb. 2010).
Boohaker et al., "The Use of Therapeutic Peptides to Target and to Kill Cancer Celis," *Curr Med Chem.*, vol. 19, pp. 3794-3804 (2012).
Boyle et al., Squaring the Circle in Peptide Assembly: From Fibers to Discrete Nanostructures by de Novo Design, *J. Am. Chem. Soc.*, vol. 134, pp. 15457-15467 (2012).
Brown, "Metal-recognition by repeating polypeptides," *Nat. Biotechnol.*, vol. 15, pp. 269-272 (1997).
Burgess et al., "Modular Design of Self-Assembling Peptide-Based Nanotubes," *J. Am. Chem. Soc.*, vol. 137, pp. 10554-10562 (2015).
Chan et al., "Antisense Oligonucleotides: From Design to Therapeutic Application," *Clin. Exp. Pharmacol. Physiol.*, vol. 33, pp. 533-540 (2006).
Chen et al., Peptide-based Methods for the Prepration of Nanostructured Inorganic Materials, *Angew. Chem. Int. Ed.*, 49: 1924-1942 (2010).

(Continued)

*Primary Examiner* — Amber D Steele
(74) *Attorney, Agent, or Firm* — Foley & Lardner LLP

(57) ABSTRACT

This disclosure related to modular and programmable peptide-oligonucleotide chimeras comprising of peptide and oligonucleotide segments interlinked by an organic core are presented and their assembly as morphologically-tunable soft materials, for example, nanostructure compositions comprising a plurality of compounds comprising a peptide segment and an oligonucleotide segment interlinked by an organic core moiety.

21 Claims, 31 Drawing Sheets
Specification includes a Sequence Listing.

(56) References Cited

OTHER PUBLICATIONS

Cui, et al., "Self-Assembly of Peptide Amphiphiles: From Molecules to Nanostructures to Biomaterials," *Biopolymers*, vol. 94, No. 1, pp. 1-18 (2010).

Cui et al., "Amino Acid Sequence in Constitutionally Isomeric Tetrapeptide Amphiphiles Dictates Architecture of One-Dimensional Nanostructures," *J. Am. Chem. Soc.*, vol. 136, No. 35, pp. 12461-12468 (2014).

De Santis, et al., "Peptide self-assembly for nanomaterials: the old new kid on the block," *Chem. Soc. Rev.*, vol. 44, pp. 8288-8300 (2015).

Dietz, et al., "Folding DNA into Twisted and Curved Nanoscale Shapes," *Science*, vol. 325, pp. 725-730 (2009).

Douglas, et al., "Self-assembly of DNA into nanoscale three-dimensional shapes," *Nature*, vol. 459, pp. 414-418 (2009).

Fletcher, et al., "Self-Assembling Cages from Coiled-Coil Peptide Modules," *Science*, vol. 340, pp. 595-599 (2013).

Gour et al., "Self-assembling DNA-peptide hybrids: morphological consequences of oligonucleotide grafting to a pathogenic amyloid fibrils forming dipeptide," vol. 48, pp. 5440-5442 (2012).

Gour et al., "Label-free, optical sensing of the supramolecular assembly into fibrils of a ditryptophan-DNA hybrid," *Chem. Commun.*, vol. 50, pp. 6863-6865 (2014).

Hamley, "Self-Assembly of Amphiphilic Peptides," *Soft Matter*, vol. 7, pp. 4122-4138 (2011).

Han, et al., "DNA origami with complex curvatures in three-dimensional space," *Science*, vol. 332, pp. 342-346 (2011).

Hartgerink, et al., "Self-Assembling Peptide Nanotubes," *J. Am. Chem. Soc.*, vol. 118, No. 1, pp. 43-50 (1996).

Humenik, et al., "Nanomaterial Building Blocks Based on Spider Silk-Oligonucleotide Conjugates," *ACS Nano*, vol. 8, pp. 1342-1349 (2014).

Huisgen, R., 1,3-Dipolare Cycloadditionen—Ruckschau und Ausblick. *Angewandte Chemie-International Edition*, 75 (13): 604-637 (1963)[Abstract].

Hurst et al., "Maximizing DNA Loading on a Range of Gold Nanoparticle Sizes," *Analytical Chemistry*, 78 (24): 8313-8318 (2006).

Jones et al., "Nanomaterials. Programmable materials and the nature of the DNA bond," *Science*, vol. 347, p. 6224, (Feb. 2015).

Ke et al., "Three-Dimensional Structures Self-Assembled from DNA Bricks," *Science*, vol. 338, pp. 1177-1183 (Nov. 2012).

Korevaar, et al., "Pathway Selection in Peptide Amphiphile Assembly," *J. Am. Chem. Soc.*, vol. 136(24) pp. 8540-8543 (2014).

Kye et al., *Angew. Chem. Int. Ed.*, 55: 12003-12007 (2016).

Lou, et al., Peptide-oligonucleotide conjugates as nanoscale building blocks for assembly of an artificial three-helix protein mimic, Nat. Commun., vol. 7, 9 pages (2016).

Macfarlane, et al., "Nanoparticle superlattice engineering with DNA," Science, vol. 334 (6053) pp. 204-208 (Oct. 2011).

Magnotti, et al., "Self-Assembly of an α-Helical Peptide into a Crystalline Two-Dimensional Nanoporous Framework," *J. Am. Chem. Soc.*, vol. 16274-16282 (Dec. 2016).

Miller, et al., "Versatile 5'-Functionalization of Oligonucleotides on Solid Support: Amines, Azides, Thiols, and Thioethers via Phosphorus Chemistry," *J. Org. Chem.*, vol. 69, No. 7, pp. 2404-2410 (2004).

Nangreave, et al., "DNA origami: A History and current Perspective," vol. 14, Issue 5, pp. 608-615 (Oct. 2010).

Nykypanchuk, et al., "DNA-Guided crystallization of Colloidal Nanoparticles," *Nature*, vol. 451, pp. 549-552 (Jan. 2008).

Park, et al., "DNA-programmable nanoparticle crystallization," *Nature*, vol. 451, pp. 553-556 (2008).

Rostovtsev, et al., "A Stepwise Huisgen Cycloaddition Process: Copper(I)-Catalyzed Regioselective 'Ligation' of Azides and Terminal Alkynes," *Angew. Chem. Int. Ed.*, vol. 41 (14), pp. 2596-2599 (2002).

Rothemund, "Folding DNA to Create Nanoscale Shapes and Patterns," *Nature*, vol. 440, pp. 297-302 (2006).

Sacca, "DNA Origami: The Art of Folding DNA," *Angew. Chem. Int. Ed.*, vol. 51, pp. 58-66 (2012).

Schreiber, et al., "Hierarchical assembly of metal nanoparticles, quantum dots and organic dyes using DNA origami scaffolds," *Nature Nanotechnology*, vol. 9, pp. 74-78 (2014).

Smith, et al., "A thermodynamic scale for the beta-sheet forming tendencies of the amino acids," *Biochemistry*, vol. 33, No. 18, pp. 5510-5517 (May 1994).

Song, et al., "Expeditious Synthesis and Assembly of Sub-100 nm Hollow Spherical Gold Nanoparticle Superstructures," *J. Am. Chem. Soc.*, vol. 132, No. 40, pp. 14033-14035 (Oct. 2010).

Stein, et al., "Antisense Oligonucleotides as Therapeutic Agents—Is the Bullet Really Magical?," *Science*, vol. 261, pp. 1004-1012 (1993).

Thaner, et al., "Facile One-Step Solid-Phase Synthesis of Multitopic Organic-DNA Hybrids via "Click" Chemistry," *Chemical Science*, vol. 5, pp. 1091-1096 (2014).

Tinland, B., et al., Persistence Length of Single-Stranded DNA. *Macromolecules*, vol. 30 (19), 5763-5765 (1997).

Torring, et al., "DNA Origami: A quantum Leap for Self-Assembly of Complex Structures," *Chem. Soc. Rev.*, vol. 40, No. 12, pp. 5636-5646 (Dec. 2011).

Tung, "Preparations and Applications of Peptide—Oligonucleotide Conjugates," *Bioconjugate Chem.*, vol. 11, pp. 605-618 (2000).

Ulijn, et al., "Designing Peptide based Nanomaterials," *Chem. Soc. Rev.*, vol. 37, pp. 664-675 (2008).

Vives et al., "Cell-penetrating and cell-targeting peptides in drug delivery," Biochem Biophys. Acta Rev. Cancer, vol. 1786, pp. 126-138 (2008).

Wei et al., "Complex shapes self-assembled from single-stranded DNA tiles," *Nature*, vol. 485 (7400) pp. 623-626 (2012).

Whaley, et al., "Selection of peptides with semiconductor binding specificity for directed nanocrystal assembly," vol. 405, pp. 665-668 (2000).

Zhang, et al., "Selection and Application of Peptide-Binding Peptides," *Nat. Biotechnol.*, vol. 18, pp. 71-74 (2000).

Zhang et al., "Complex wireframe DNA origami nanostructures with multi-arm junction vertices," *Nat. Nanotech*, vol. 10, pp. 779-784 (2015).

Zhao, et al., "Molecular self-assembly and applications of designer peptideamphiphiles," *Chem. Soc. Rev.*, vol. 39, pp. 3480-3498 (2010).

\* cited by examiner

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Ala Tyr Ser Ser Gly Ala Pro Pro Met Pro Pro Phe
1               5                   10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aacgactcat attaacaa                                                   18

<210> SEQ ID NO 3
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 3
taacgactca tattaacaa                                                   19

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Tyr Ser Ser Gly Ala Pro Pro Met Pro Pro Phe
1               5                   10
```

PEPTIDE-OLIGONUCLEOTIDE CHIMERAS (POCS) AS PROGRAMMABLE BIOMOLECULAR CONSTRUCTS FOR THE ASSEMBLY OF MORPHOLOGICALLY-TUNABLE SOFT MATERIALS

CROSS-REFERENCE TO RELATED APPLICATION

This application claims priority to U.S. Provisional Patent Application No. 62/480,176 filed Mar. 31, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 19, 2022, is named 076333-0909_SL.txt and is 1,459 bytes in size.

BACKGROUND

Few classes of material building blocks exhibit the programmability offered by nucleic acids and peptides, each of which offers a distinct set of properties from a material-assembly standpoint, each. Nucleic acids exhibit unrivalled site-specificity that is based on their sequence-specific base-pairing interactions between complementary oligonucleotides. This allows for the construction of highly intricate nanoscale architectures as demonstrated by DNA origami[1] and spherical nucleic acid-based assemblies. [Jones et al., *Science*, 347 (2015); Torring et al., *Chem. Soc. Rev.*, 40:5636-5646 (2011); B. Sacca, C. M. Niemeyer, *Angew. Chem. Int. Ed.*, 51: 58-66 (2012); Nangreave et al., *Curr. Opin. Chem. Biol.*, 14: 608-615 (2010); P. W. K. Rothemund, *Nature*, 440: 297-302 (2006); E. S. Andersen et al., *ACS Nano*, 2: 1213-1218 (2008); Rajendran et al., *ACS Nano*, 5: 665-671 (2011); Han et al., *Science*, 332: 342-346 (2011); Douglas et al., *Nature*, 459: 414-418 (2009); Ke et al., *Science*, 338: 1177-1183 (2012); Zhang et al., *Nat. Nanotech.*, 10: 779-784 (2015); Schreiber et al., *Nat. Nanotech.*, 9: 74-78 (2014); Wei et al., *Nature*, 485:623-626 2012); Dietz et al., *Science*, 325:725-730 (2009); Macfarlane et al., *Science*, 334: 204-208 (2011); Nykypanchuk et al., *Nature*, 451: 549-552 (2008); Park et al., *Nature*, 451: 553-556 (2008).] In addition, peptides have also been extensively exploited as assembly components. They exhibit highly modular assembly and substrate-recognition capabilities, drawing from their rich diversity of amino acid sequences. [E. De Santis, M. G. Ryadnov, *Chem. Soc. Rev.*, 44: 8288-8300 (2015); R. V. Ulijn, A. M. Smith, *Chem. Soc. Rev.*, 37: 664-675 (2008); Zhao et al., *Chem. Soc. Rev.*, 39: 3480-3498 (2010); I. W. Hamley, *Soft Matter*, 7: 4122-4138 (2011); Cui et al., *J. Am. Chem. Soc.*, 136: 12461-12468 (2014); Magnotti et al., *J. Am. Chem. Soc.*, 138: 16274-16282 (2016); Korevaar et al., *J. Am. Chem. Soc.*, 136: 8540-8543 (2014); Boyle et al., *J. Am. Chem. Soc.*, 134: 15457-15467 (2012); Burgess et al., *J. Am. Chem. Soc.*, 137: 10554-10562 (2015); Hartgerink et al., *J. Am. Chem. Soc.*, 118: 43-50 (1996); Fletcher et al., *Science*, 340: 595-599 (2013); Whaley et al., *Nature*, 405: 665-668 (2000); S. Brown, *Nat. Biotechnol.*, 15: 269-272 (1997); C.-L. Chen, N. L. Rosi, *Angew. Chem. Int. Ed.*, 49: 1924-1942 (2010); Zhang et al., *Nat. Biotechnol*, 18:71-74 (2000); Vives et al., *Biochim. Biophys. Acta, Rev. Cancer*, 1786: 126-138 (2008)]

For example, a 10-mer peptide built from natural amino acids can have $20^{10}$ possible sequences. It stands to reason that molecular building blocks composed of both nucleic acids and peptides would have the potential to assemble into materials that exhibit heretofore unobserved features and properties.

Peptide-oligonucleotide chimeras ("POC"s), comprising interlinked peptides and oligonucleotides around a directing core, represent a new, versatile class of building blocks having assembly characteristics and properties deriving from both biomolecular components. While biological applications of POCs have been explored [N. Venkatesan, B. H. Kim, *Chem. Rev.*, 106: 3712-3761 (2006); C.-H. Tung, S. Stein, *Bioconjugate Chem.*, 11: 605-618 (2000)], few studies have examined their potential as programmable building blocks for the construction of soft materials. [Gour et al., *Chem. Commun.*, 48: 5440-5442 (2012); Abraham et al., *Eur. Polym.* 1, 65: 268-275 (2015); Kye et al., *Angew. Chem. Int. Ed.*, 55: 12003-12007 (2016); Lou et al., *Nat. Commun.*, 7: 12294 (2016); Gour et al., *Chem. Commun.*, 50: 6863-6865 (2014); Humenik et al., *ACS Nano*, 8: 1342-1349 (2014).]

Accordingly, a need exists for POCs that are highly tunable assembly platforms where both peptide and oligonucleotide "characters" can be independently varied around a directing moiety, with better directional and multiplicity control than traditionally possible.

SUMMARY OF THE DISCLOSURE

The present disclosure relates, in part, to compounds comprising a peptide segment and an oligonucleotide segment interlinked by an organic core moiety and nanostructure compositions comprising a plurality of these compounds.

In some embodiments, the disclosure relates to a compound comprising a peptide segment and an oligonucleotide segment interlinked by an organic core moiety. In some embodiments, the compound is represented by the following formula (I):

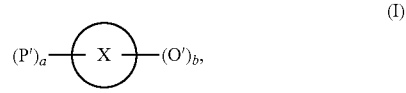

(I)

wherein P' is the peptide segment; O' is the oligonucleotide segment; X is the organic core moiety; a is 1-4 and b is 1-4. In some embodiments, the peptide segment comprises two or more natural or synthetic amino acids. In some embodiments, the peptide segment consists of natural or synthetic amino acids. In some embodiments, the peptide segment comprises about 2 to about 25 natural or synthetic amino acids.

In some embodiments, the peptide segment comprises a peptide capable of forming β-sheets. In some embodiments, the peptide segment comprises a peptide capable of effecting an assembly to form self-assembling nanoscale systems. In some embodiments, the self-assembling nanoscale system is selected from 1D fiber, a hollow sphere and a micelle-type structure. In some embodiments, the peptide segment comprises a therapeutic peptide. In some embodiments, the oligonucleotide segment comprises two or more modified or unmodified nucleosides containing natural or synthetic nucleobases and modified or unmodified internucleoside linkages. In some embodiments, the oligonucleotide segment comprises two or more modified or unmodified nucleosides comprising natural or synthetic nucleobases and modified or unmodified internucleoside linkages. In some embodiments, the oligonucleotide segment comprises an antisense oligonucleotide. In some embodiments, the organic core moiety comprises an optionally substituted aryl or heteroaryl moiety. In some embodiments, the organic core moiety comprises an optionally substituted aryl moiety. In some embodiments, the organic core moiety comprises an optionally substituted aliphatic moiety. In some embodiments, in formula (I), a and b are each 1. In some embodiments, in formula (I), a is 1 and b is 2 or more.

Other embodiments include a nanostructure composition comprising a plurality of compounds according to any of the above embodiments. In some embodiments, the nanostructure is a 1D fiber. In some embodiments, is a hollow sphere. In some embodiments, the hollow sphere comprises a monolayer of the plurality of compounds with the oligonucleotide portions directed towards the outer surface. In some embodiments, the hollow sphere has a diameter of about 10 to about 500 nm.

BRIEF DESCRIPTION OF THE DRAWINGS

FIG. 3(a) TEM and FIG. 3(b) SEM images of $PO_{18}C$ vesicles assembled in 50 mM $CaCl_2$ after 15-0 hrs. FIG. 3(c) AFM image of $PO_{18}C$ vesicles deposited on unfunctionalized mica. FIG. 3(d) AFM image of a single vesicle and FIG. 3(e) corresponding height profile along the dashed line shown in d. FIG. 3(f) Phase image of the vesicle shown in d, revealing the different surface profiles between the periphery and the interior. FIG. 3(g) TEM images of gold nanoparticle-decorated vesicles after addition of 15 nm gold nanoparticles functionalized with complementary $O_{18}$ sequences to a solution of $PO_{18}C$ vesicles. FIG. 3(h) Proposed assembly model of $PO_{18}C$ vesicles.

FIG. 12(a) UV-vis spectrum of free 15 nm gold nanoparticles functionalized with complementary 018 sequence (upper peak line) and gold nanoparticle-decorated vesicles after addition of the complementary functionalized gold nanoparticles to a solution containing $PO_{18}C$ vesicles (lower peak line). FIG. 12(b) Corresponding TEM image of the gold nanoparticle-decorated $PO_{18}C$ vesicles after 2 hrs.

FIG. 14(a) Greater charge shielding can allow for tighter packing of POCs, which can lead to fiber formation. FIG. 14(b) Greater repulsion due to less charge shielding favors the formation of vesicles.

(FIG. 19c-e) Zoomed-in TEM images of the dashed boxes shown in b (the border correspond to the dashed boxes starting with "c" in the upper middle, then "d" and "e" in clockwise fashion).

(FIG. 20a,b) TEM images 2 hrs. after addition of 5 nm gold nanoparticles (functionalized with complementary 6mer sequence) to a solution containing $PO_6C$ fibers in 50 mM $CaCl_2$). (FIG. 20c) UV-Vis spectrum of free 5 nm gold nanoparticles functionalized with complementary 6mer sequence (higher peak line) and 2 hrs. after addition to $PO_6C$ fibers (lower peak line). The position of the LSPR band remains unchanged. The difference in signal intensity is due to different solution concentrations.

(FIG. 22a) TEM images of $PO_6C$ fibers assembled in 50 mM $CaCl_2$) after 15-20 hrs. (FIG. 22b) FTIR spectra of $PO_{18}C$ vesicles (lower peak line) and $PO_6C$ fibers (higher peak line) assembled in 50 mM $CaCl_2$).

(FIG. 23a) The charge ratio value is the ratio of positive to negative charges of the assembly solution (N=number of oligonucleotide bases; the '+2' results from the azido-functionalized T residue, FIG. 51, and the deprotonated COO-terminus of the peptide). (FIG. 23b) The charge ratio of the assembly solution as a function of $CaCl_2$) concentration and oligonucleotide length. TEM images of $PO_{18}C$ vesicles (FIG. 23c) before and (FIG. 23d) after conc. $CaCl_2$ addition.

DETAILED DESCRIPTION

1. Peptide-Oligonucleotide Chimeras

Figure 1:
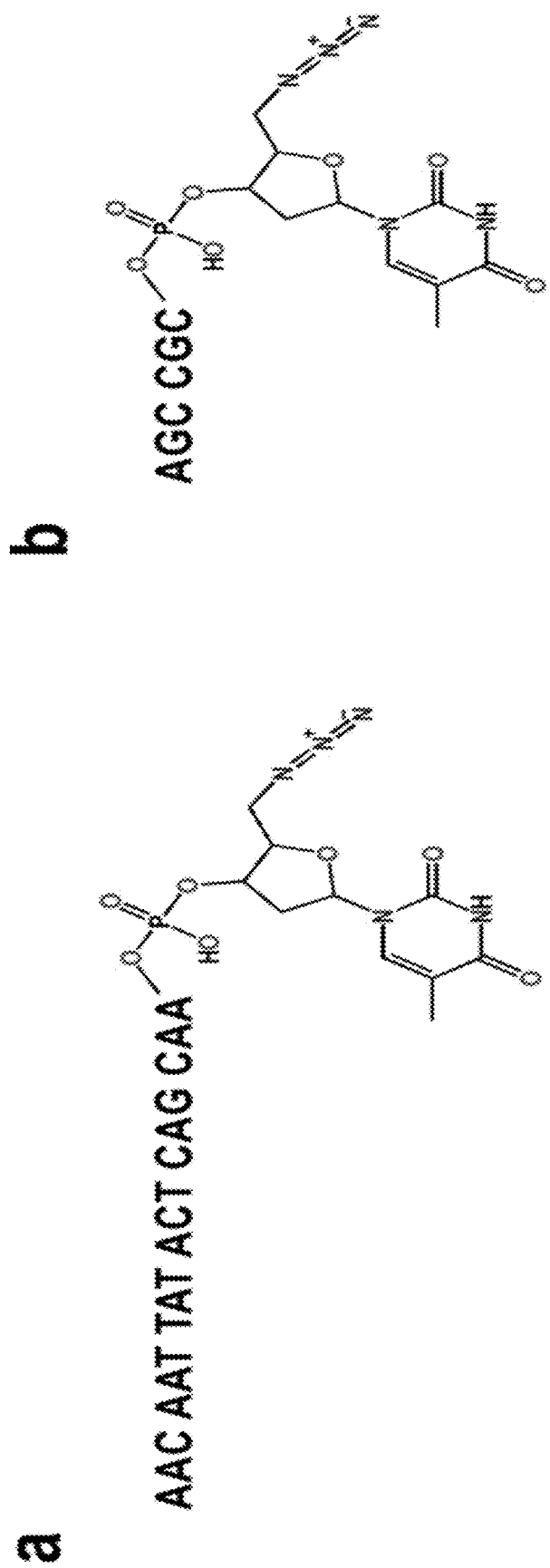
FIG. 1: Structure of an embodiment of the disclosure of (FIG. 1a) a18-base azido-modified oligonucleotide (SEQ ID NO: 2; sequence is depicted in the figure in the 3' to 5' orientation and disclosed herein as 5'-AAC GAC TCA TAT TAA CAA-3') ($O_{18}$—$N_3$) and (FIG. 1b) a 6-base azidomodified oligonucleotide ($O_6$—$N_3$).
Figure 2:
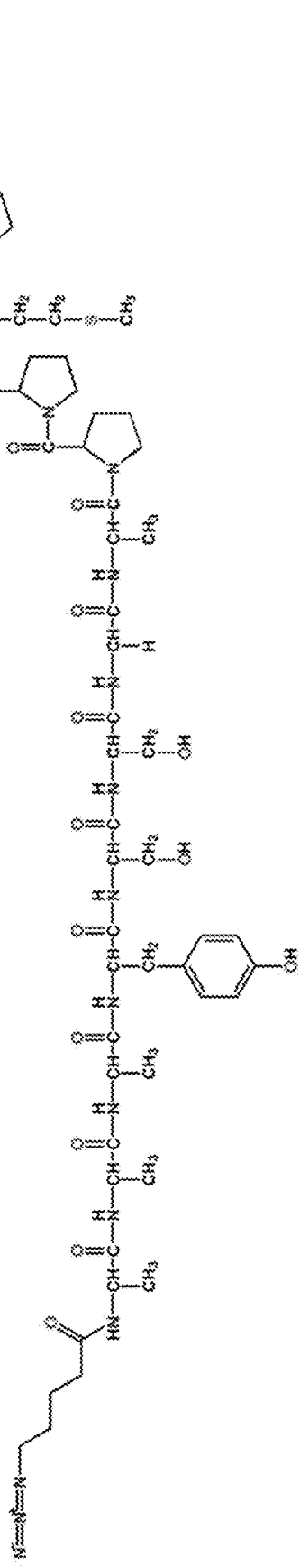
FIG. 2: Chemical structure of an azido-modified peptide ($N_3$—$C_4H_8$CO-AAAYSSGAPPMPPF (SEQ ID NO: 1)) of the disclosure.

The present disclosure includes peptide-oligonucleotide chimeras ("POC"s). In some embodiments, these POCs include a peptide segment and an oligonucleotide segment interlinked by an organic core moiety. These POCs may be modular and/or programmable to provide a desired functionality and/or assembly to produce highly tunable soft nanoscale materials.

In some embodiments, the POC comprises a peptide segment and an oligonucleotide segment interlinked by an organic core moiety. In certain embodiments, the POC comprises more than one peptide segment and/or oligonucleotide segment (e.g., 2, 3, 4, or 5 peptide segments or oligonucleotide segment). For example, the POC may be represented by the following formula (I):

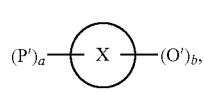

(I)

wherein P' is the peptide segment; O' is the oligonucleotide segment; X is the organic core moiety; a is 1-4 and b is 1-4.

The peptide segment is not particularly limited. It includes at least two amino acid moieties, for example known natural or synthetic amino acids. As noted above, in some embodiments, the peptide segment comprises about 2 to about 25 natural or synthetic amino acids. In other embodiments, the peptide comprises about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 natural or synthetic amino acids.

The peptide may have an assembly role or a therapeutic role. In other words, the peptide can effect an assembly role under certain conditions (e.g., self-assembling nanoscale systems). These types of peptide sequences have been discussed in the art, for example, in Ulijn, R. V.; Smith, A. M. *Chem. Soc. Rev.,* 37: 664-675 (2008); Cui et al. *Pep. Sci.,* 94: 1-18 (2010); Song et al., *J. Am. Chem. Soc.,* 132: 14033-14035 (2010). Some embodiments include a peptide segment that has a therapeutic effect, for example, a cell-penetrating and/or cell-targeting peptides. These types of peptide sequences have been discussed in the art, for example, in Vives et al., Biochim. Biophys. *Acta, Rev. Cancer,* 1786: 126-138 (2008); Boohaker et al., *Curr Med Chem.,* 19: 3794-3804 (2012); Bahar, A. A.; Ren, D., *Pharmaceutical,* 6: 1543-1575 (2013). These peptides may also be selected from classes of peptides that have been selected or designed to bind to specific substrates, such as organic/inorganic materials/surfaces/nanoparticles, such as those described in the art: Chen et al., *Angew. Chem. Int. Ed,* 49: 1924-1942 (2010), and Dickerson et. al., *Chem. Rev.,* 108: 4935-4978 (2008).

Some embodiments of the peptide segment include peptides with a known ability to assemble into various structures (e.g. fibers, vesicles) when conjugated to an organic molecule at its N-terminus, such as AAAYSSGAPPMPPF (SEQ ID NO: 1) or peptide segments described in Cui et al. (cited previously). Additional embodiments, include peptide moieties known to assemble into β-sheets, such as when a hydrophobic R-group is attached to the alanine residue of AAAYSSGAPPMPPF (SEQ ID NO: 1). Other embodiments of the peptide segment include peptides bearing sequences of amino acids that have a propensity to form β-sheets; these amino acids include, but are not limited to, tyrosine, phenylalanine, valine, isoleucine, tryptophan, and threonine (from Smith et al., *Biochemistry,* 33: 5510-5517 (1994)).

The oligonucleotide segment is not particularly limited. It includes at least two nucleotides, which may include modified or unmodified nucleosides containing natural or synthetic nucleobases and modified or unmodified internucleoside linkages (e.g., a phosphodiester linkage or a modified internucleoside linkage). Unmodified nucleosides include DNA and RNA nucleosides. Modified nucleosides have been described in the art, for example, 2'-O-methoxyethyl, 2'-O-methyl, 2'-fluoro, 'locked' nucleic acids, bicyclic nucleic acids, cyclohexene nucleic acids, tricycle nucleic acids. Likewise, synthetic nucleobases have been described in the art, for example, $C_5$-propynyl pyrimidine bases. Further, modified internucleoside linkages have been described in the art, for example, phosphorothioate, thiophosphoramidate, morpholino, and peptide nucleic acid linkages.

Some embodiments of the oligonucleotide segment include, oligonucleotides such as those described in U.S. Pat. No. 8,999,947. Additional oligonucleotide segments include, e.g., those with antisense properties, such as those in Chan et al., *Clin. Exp. Pharmacol. Physiol.,* 33:533-540 (2006); Uhlmann, E.; Peyman, A. *Chem. Rev.,* 90: 543-584 (1990); Stein, C. A.; Cheng Y.-C., *Science,* 261:1004-1012 (1993); Bennet, C. F.; Swayze, E. E., *Annu. Rev. Pharmacol. Toxicol.,* 50:259-293 (2010). Specific examples include, e.g., various antisense oligonucleotides that have reached clinical trials, including those in Table 1 of Chan et al. and Table 2 of Bennet et. al.

The organic core moiety is not particularly limited so long as it is capable of covalently binding to the oligonucleotide segment and the peptide segment. In some embodiments the organic core moiety may be comprised of an optionally substituted aryl or heteroaryl moiety, such as phenyl, napthyl, biphenyl, substituted aryls, polyaromatic hydrocarbons, and the like. In other embodiments, the organic core moiety may be comprised of an optionally substituted aliphatic moiety, e.g., alkyl, alkenyl or alkynyl moiety).

2. POC Structures

The POCs may be modular and/or programmable to provide a desired functionality and/or assembly to produce highly tunable soft nanoscale materials. Some embodiments include POC structures, comprising a plurality of POCs assembled into a nanostructure, such as a molecular, supramolecular, polymer, clusters, for example, a 1D fiber or a hollow sphere or a micelle-type structure.

In some embodiments, the POC structure is a hollow sphere. The hollow sphere may comprise a POC monolayer with the oligonucleotides directed towards the outer surface, or a POC monolayer with the oligonucleotides directed towards the inner surface. In some embodiments, the hollow sphere may contain a composition within the sphere, such as a therapeutic compound or other composition. In some embodiments, the hollow sphere has a diameter of about 10, about 20, about 30, about 40, about 50, about 100, about 150, about 200, about 250, about 300, about 400, about 500, about 600, about 700, about 800, about 900, or about 1000 nm. The diameter may be controlled, e.g., by the length of the POC structure.

In some embodiments, the POC structure is a 1D fiber. The 1D fiber may comprise twisted 1D fibers or fiber aggregates. In some embodiments, the fibers are composed of several individual bundled strands. In some embodiments, the oligonucleotides within the fibers are relatively inaccessible. In some embodiments, the oligonucleotide segment of the POC is exposed to the aqueous assembly medium.

3. POC Structure Compositions and Methods of Production

Figure 23:
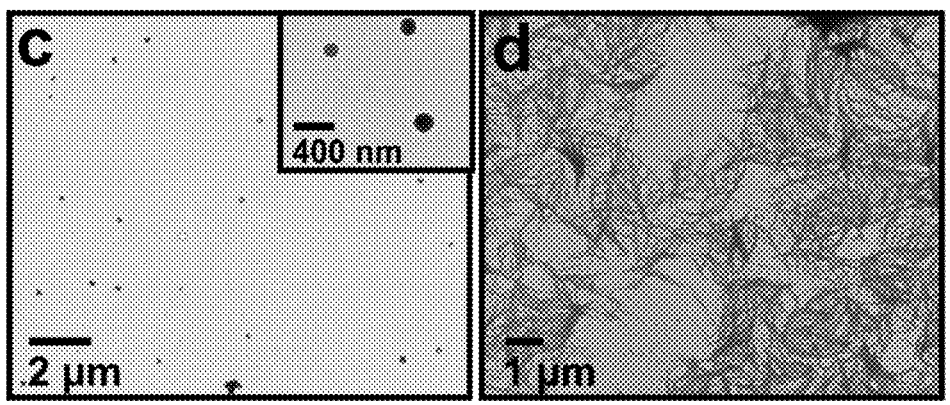
FIG. 23.
Figure 24:
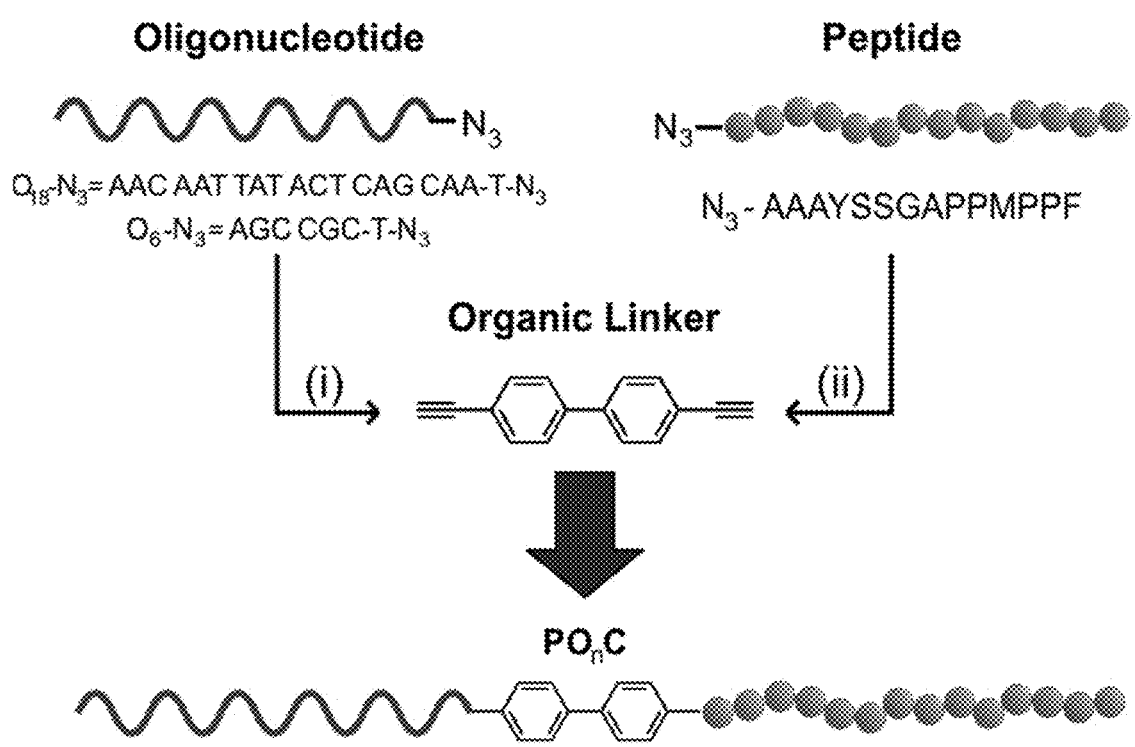
FIG. 24: shows an embodiment of modular synthesis of POCs: i) covalent attachment of an azido-modified oligonucleotide sequence to a biphenyl organic linker followed by ii) covalent attachment of an azido-modified peptide. Figure discloses SEQ ID NOS 3 and 1, respectively in order of appearance; SEQ ID NO: 3 is depicted in the figure in the 3' to 5' orientation and disclosed herein as 5'-T AAC GAC TCA TAT TAA CAA-3'.

In some embodiments, the POC structure is assembled in aqueous media optionally containing a charge-shielding cation. For example, in some embodiments, the cation may consist of a Group I or Group II cation, such as $Ca^{2+}$. The cation may be present at a specific concentration, for example, about 10, about 50, about 100, about 150, about 200, about 250, or about 300 mM, or more. In some embodiments, the charge ratio of the charge-shielding cation to the negative charge in the POCs is about 2 to about 500, or about 5, about 10, about 25, about 30, about 40, about 50, about 60, about 70, about 80, about 90, about 100, about 110, about 120, about 130, about 140, about 150, about 200, about 250, about 300, about 400, or about 500 or more (see, e.g., FIG. 23). Accordingly, some embodiments include a method of changing the POC structure by altering the charge ratio of the environment that the POC is in (e.g., from hollow sphere to 1D fiver, or vice versa). In some embodiments, the POC design is altered by introducing a specific chemical effector into the system in the form of, e.g., a complementary oligonucleotide, which may change the rigidity of the POC. In other embodiments, the hybridization would affect the assembly behavior by decreasing the charge ratio.

In some embodiments, the POCs in solution are treated to denature any non-specific initial aggregation prior to assembly through various means such as heat.

Figure 3:
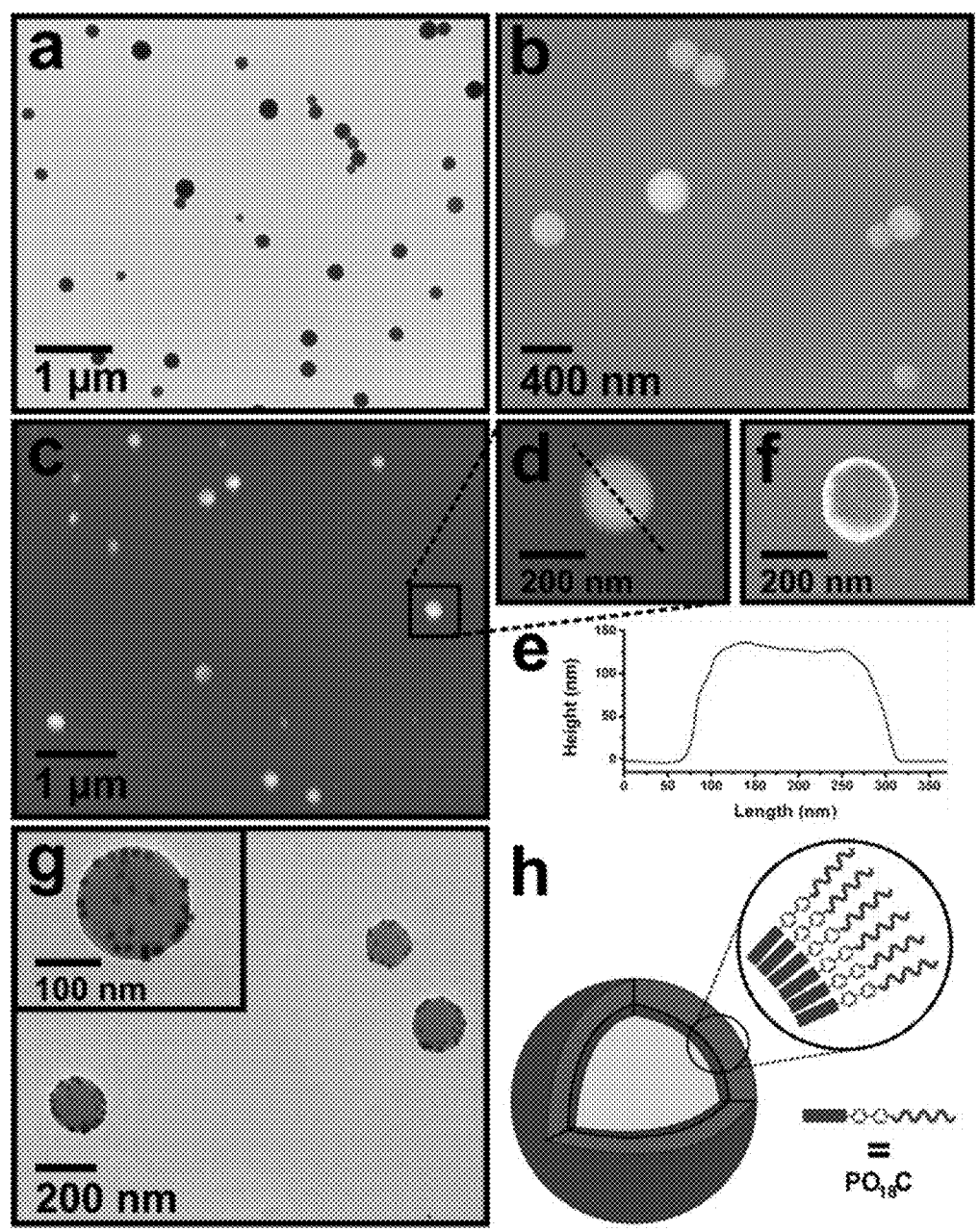
FIG. 3.
Figure 4:
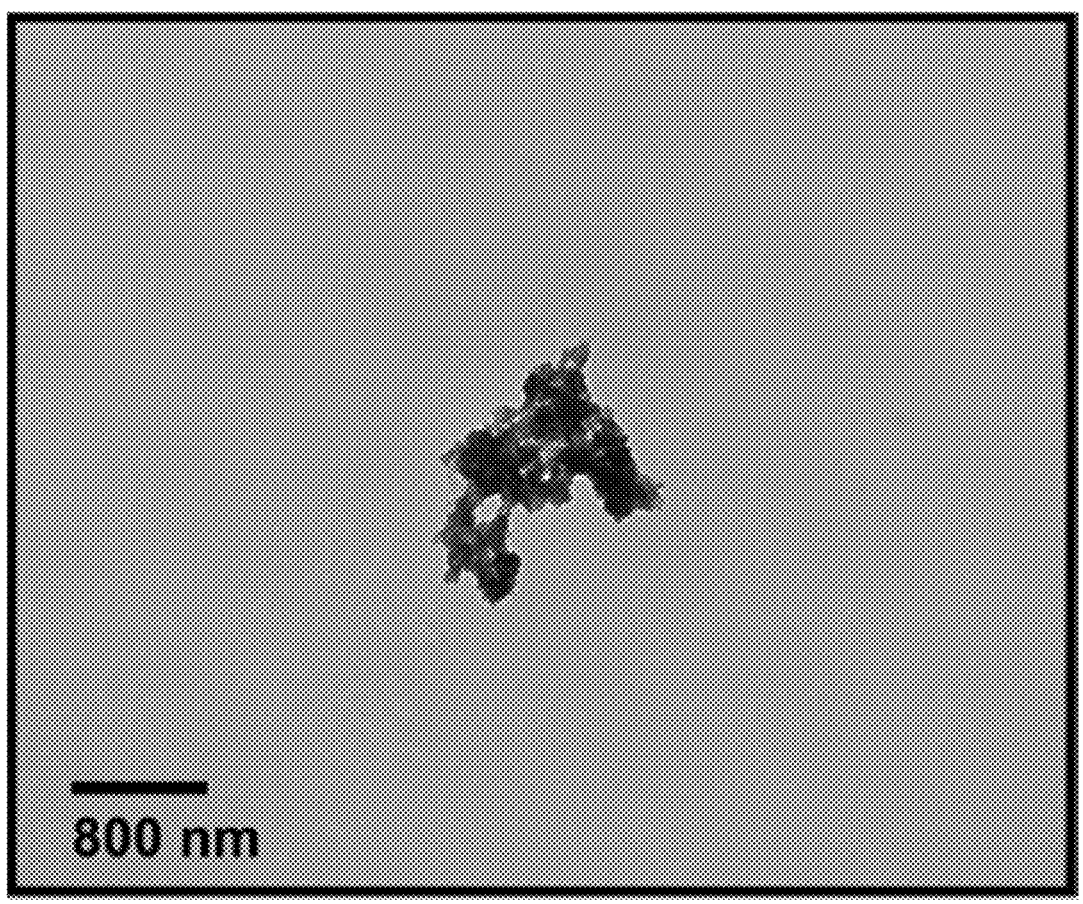
FIG. 4: TEM image of 500 μM $PO_{18}C$ in 10 mM $CaCl_2$ after 15-20 hrs. Very few assembled structures were observed.
Figure 5:
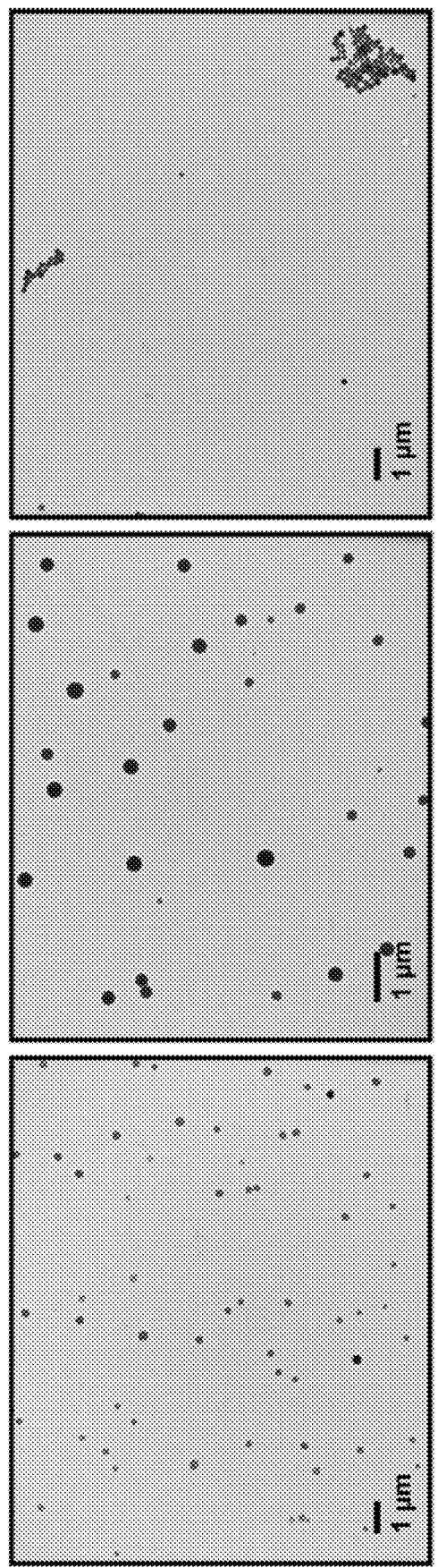
FIG. 5: TEM images of 500 μM $PO_{18}C$ in 50 mM $CaCl_2$ after 15-20 hrs. Spherical assemblies were observed.
Figure 6:
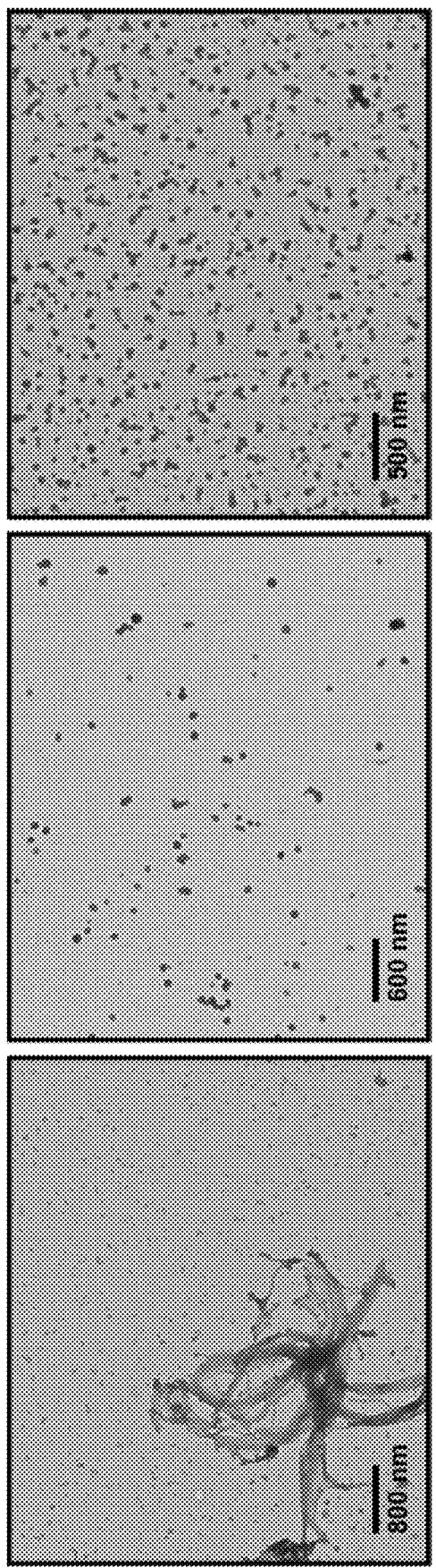
FIG. 6: TEM images of 500 μM $PO_{18}C$ in 150 mM $CaCl_2$ after 15-20 hrs. Spherical/pseudospherical assemblies were the major products. Few fiber assemblies were also observed.
Figure 7:
FIG. 7: TEM images of 500 μM $PO_{18}C$ in 300 mM $CaCl_2$ after 15-20 hrs. Fibers were observed.
Figure 8:
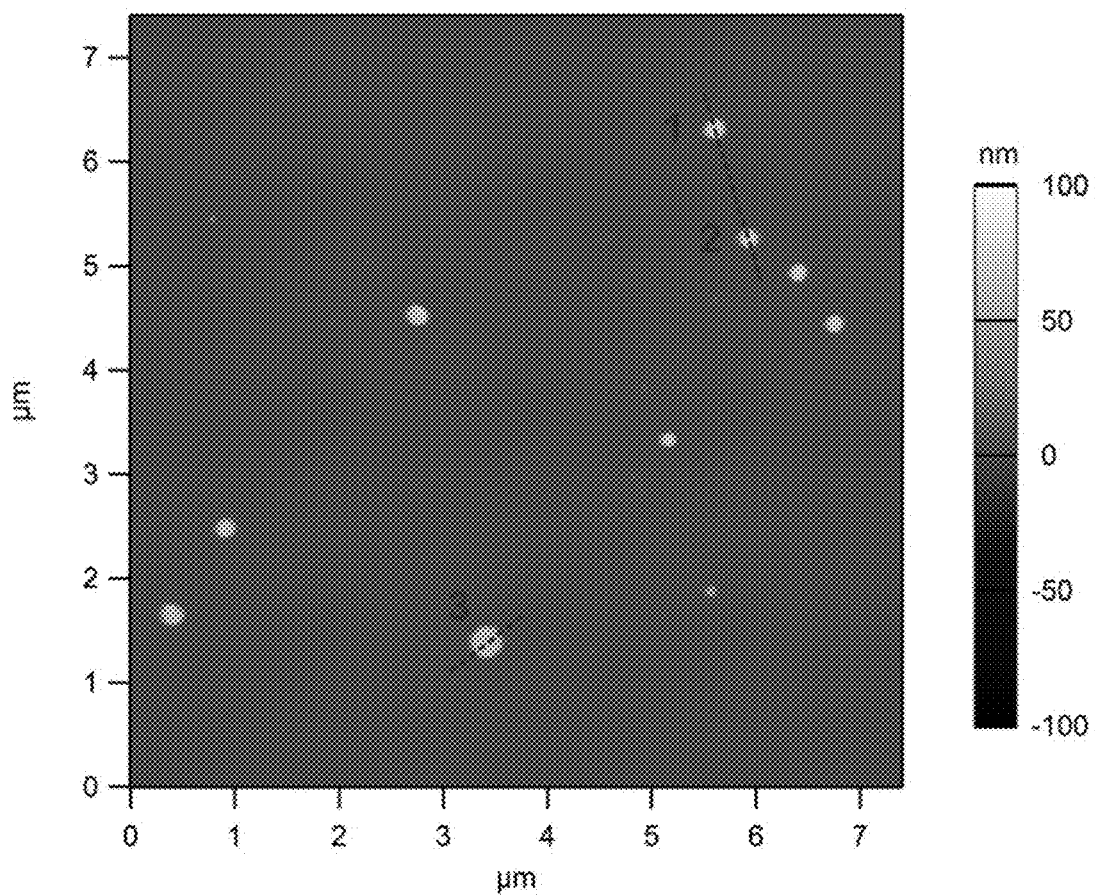
FIG. 8: AFM images with labeled vesicles and their corresponding height traces. In general, larger vesicles appear to flatten more than smaller vesicles.
Figure 8:
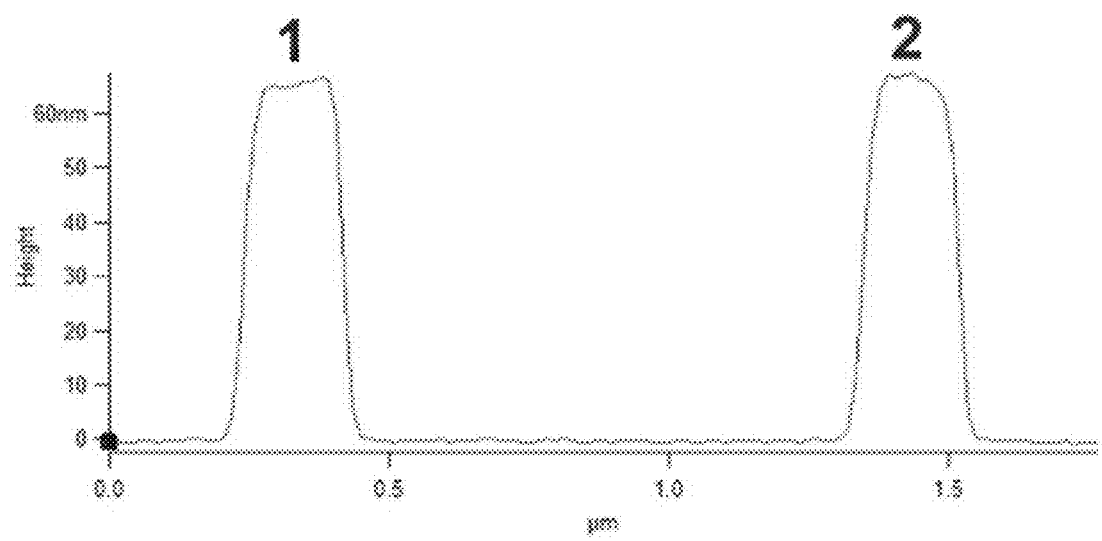
Figure 8:
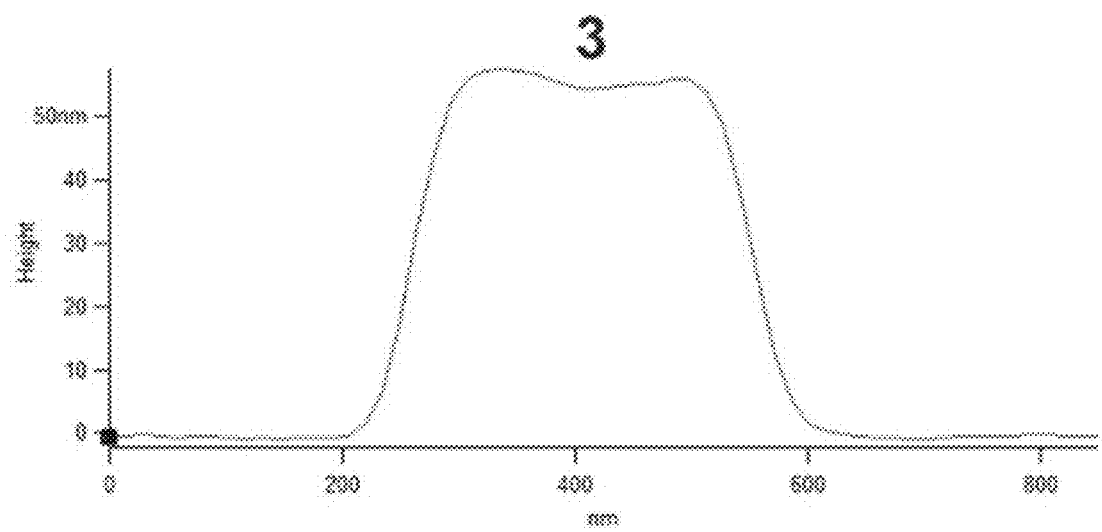
Figure 8:
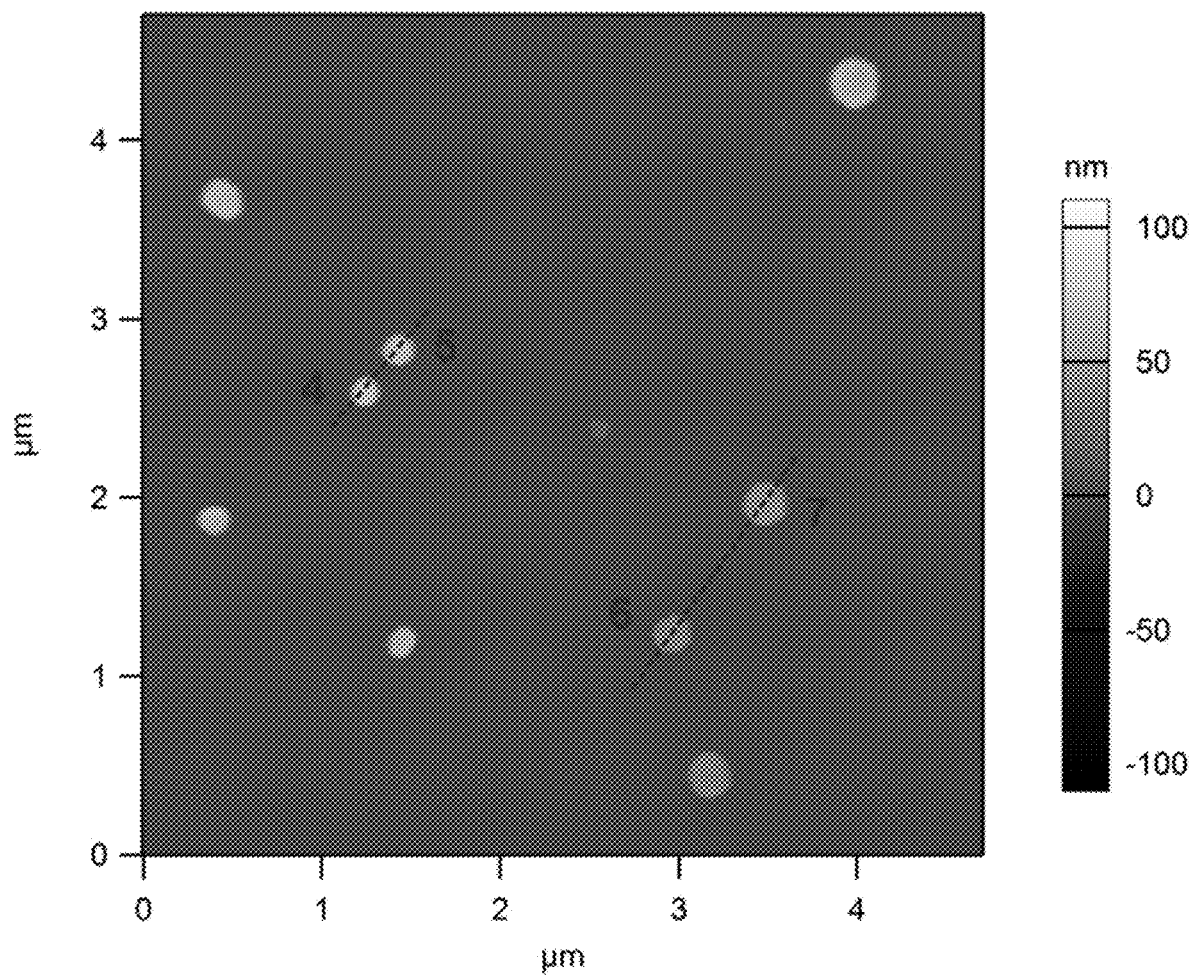
Figure 8:
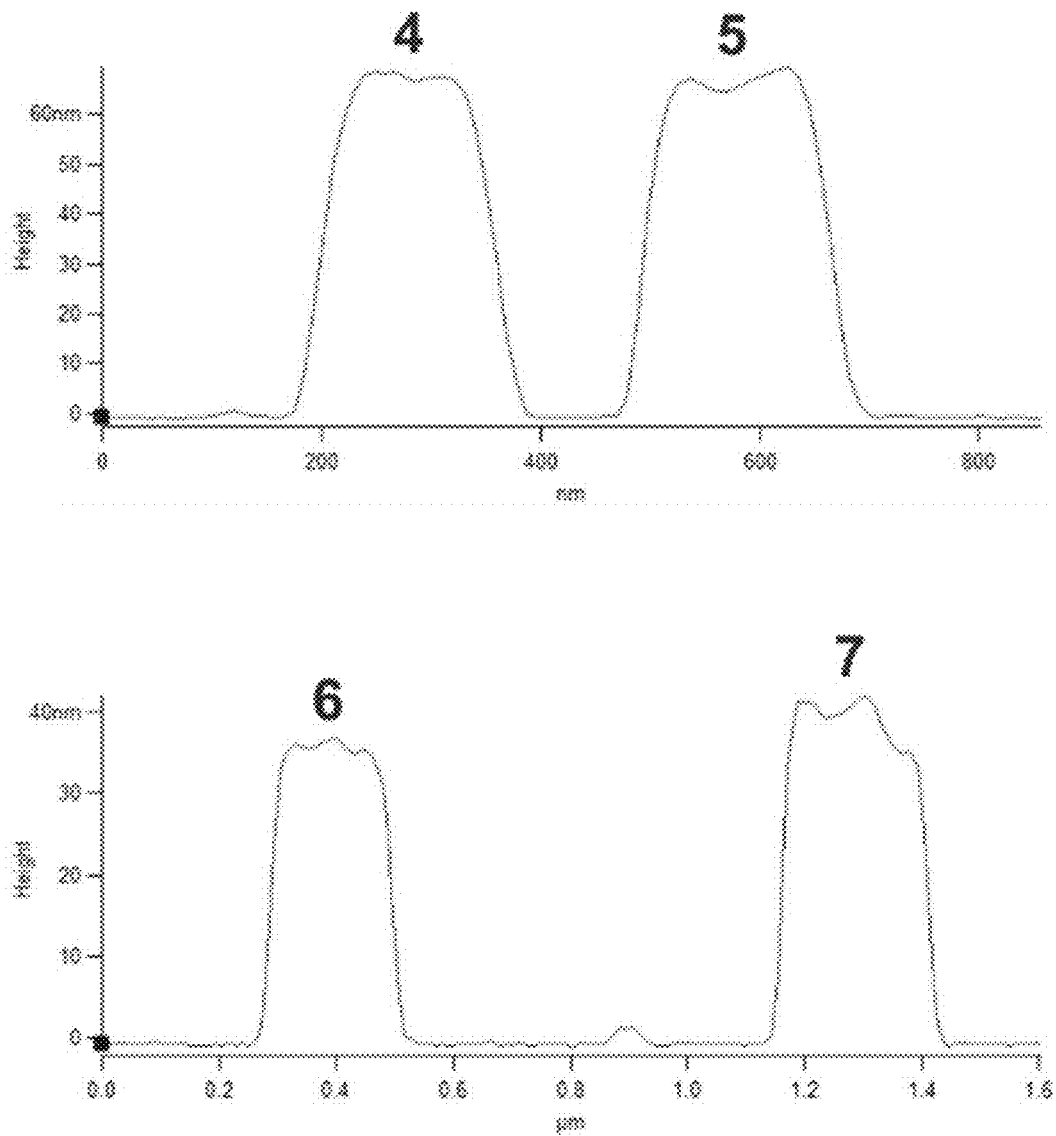
Figure 9:
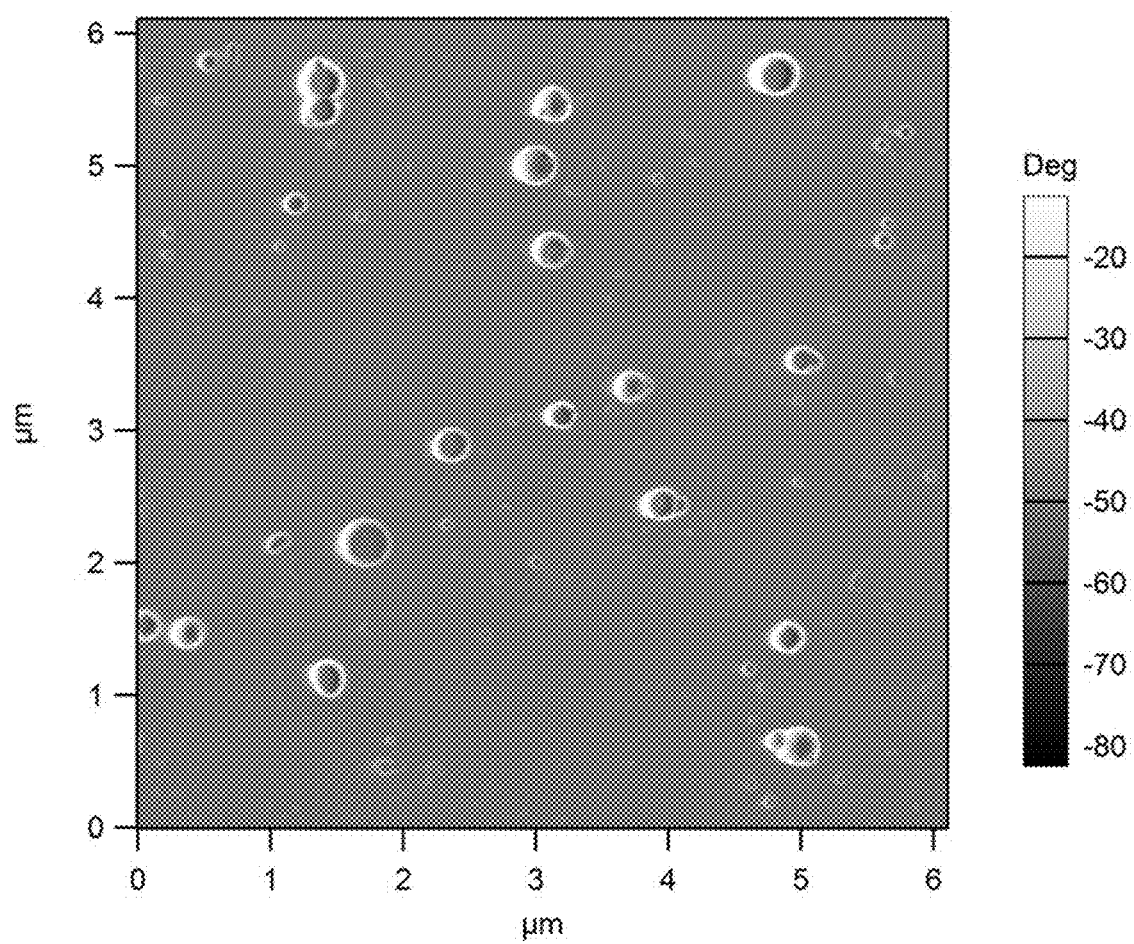
FIG. 9: Phase image of the $PO_{18}C$ vesicles revealing the different deformation response between the sphere edge and sphere center.
Figure 10:
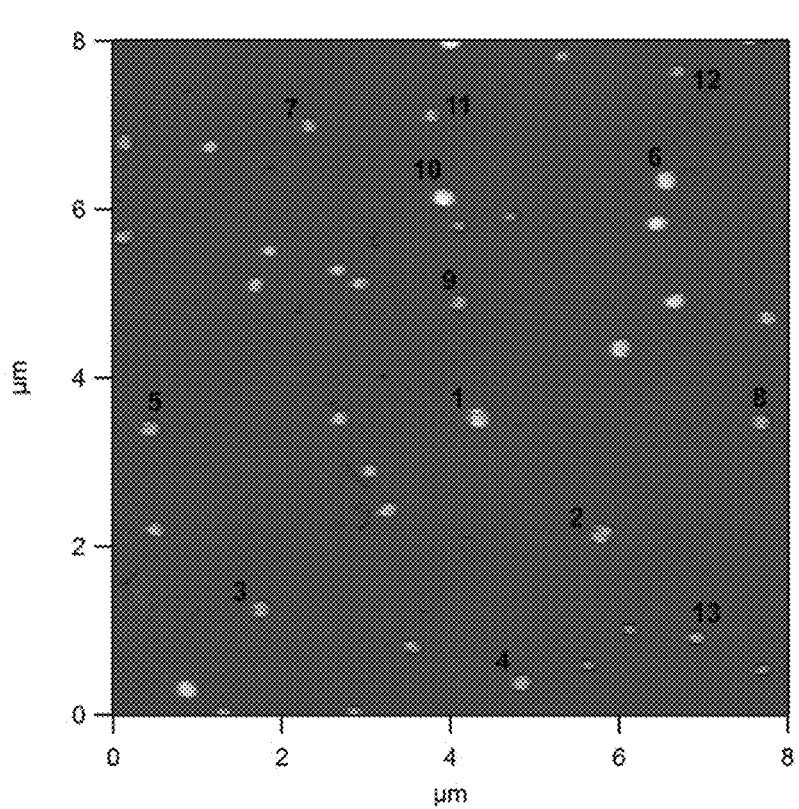
FIG. 10: AFM image of vesicles on a TEM grid after exposure to the high-vacuum TEM environment. Labeled vesicles and their corresponding height traces reveal a height of approximately 30 nm. A majority of the vesicles appear to flatten completely, except for a few that retained more of their shape (e.g. spheres 6 and 10).
Figure 10:
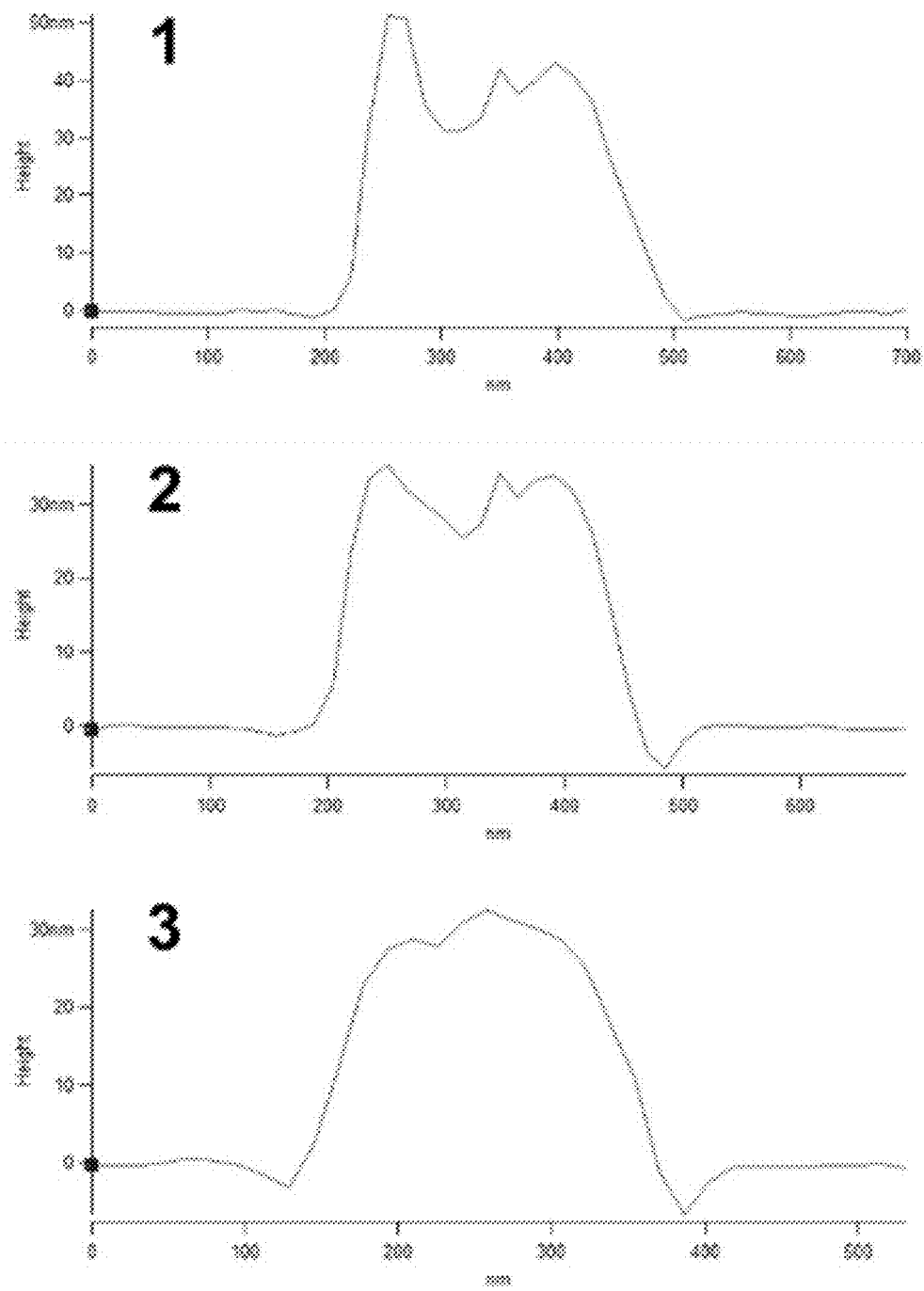
Figure 10:
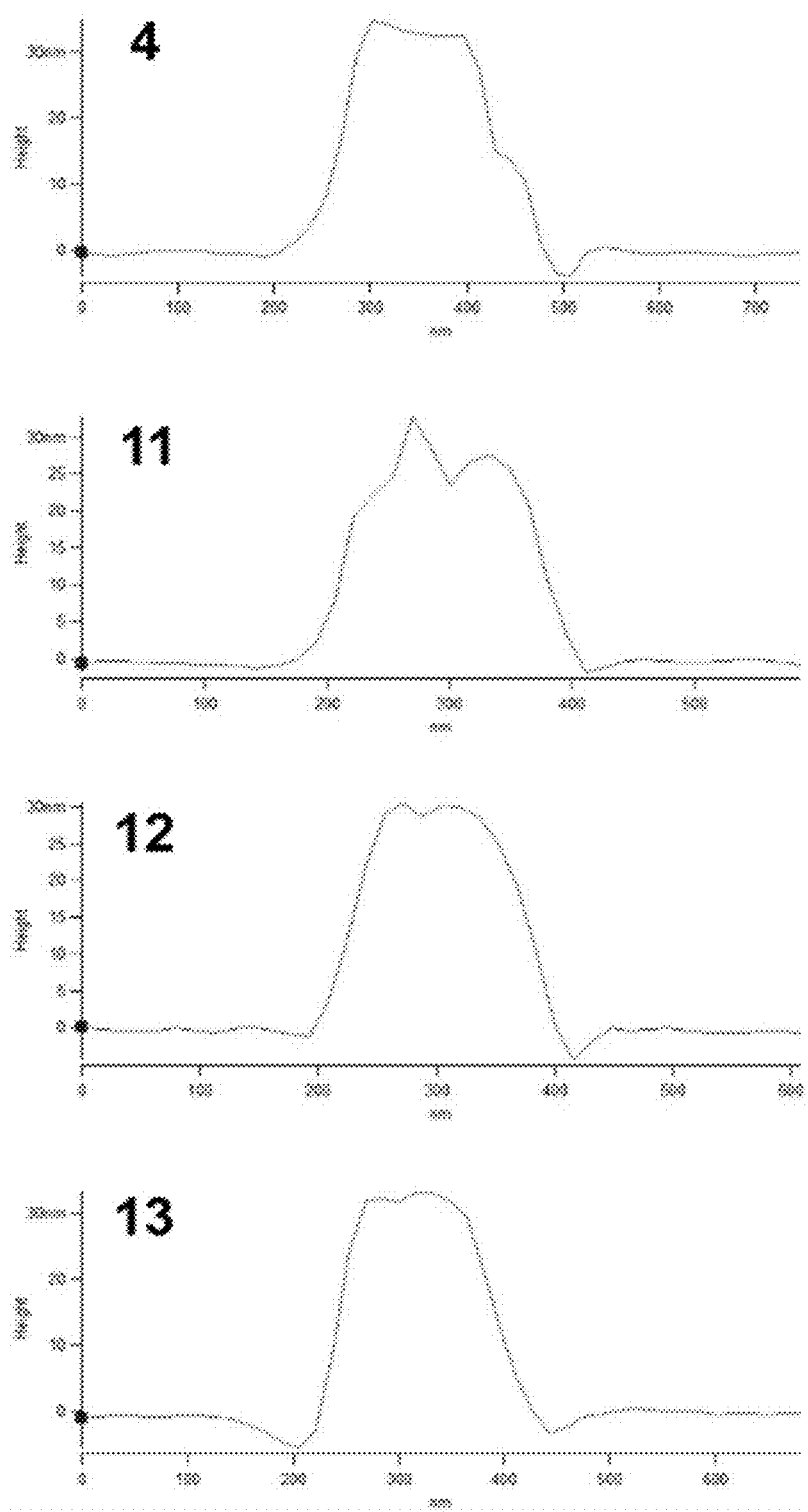
Figure 10:
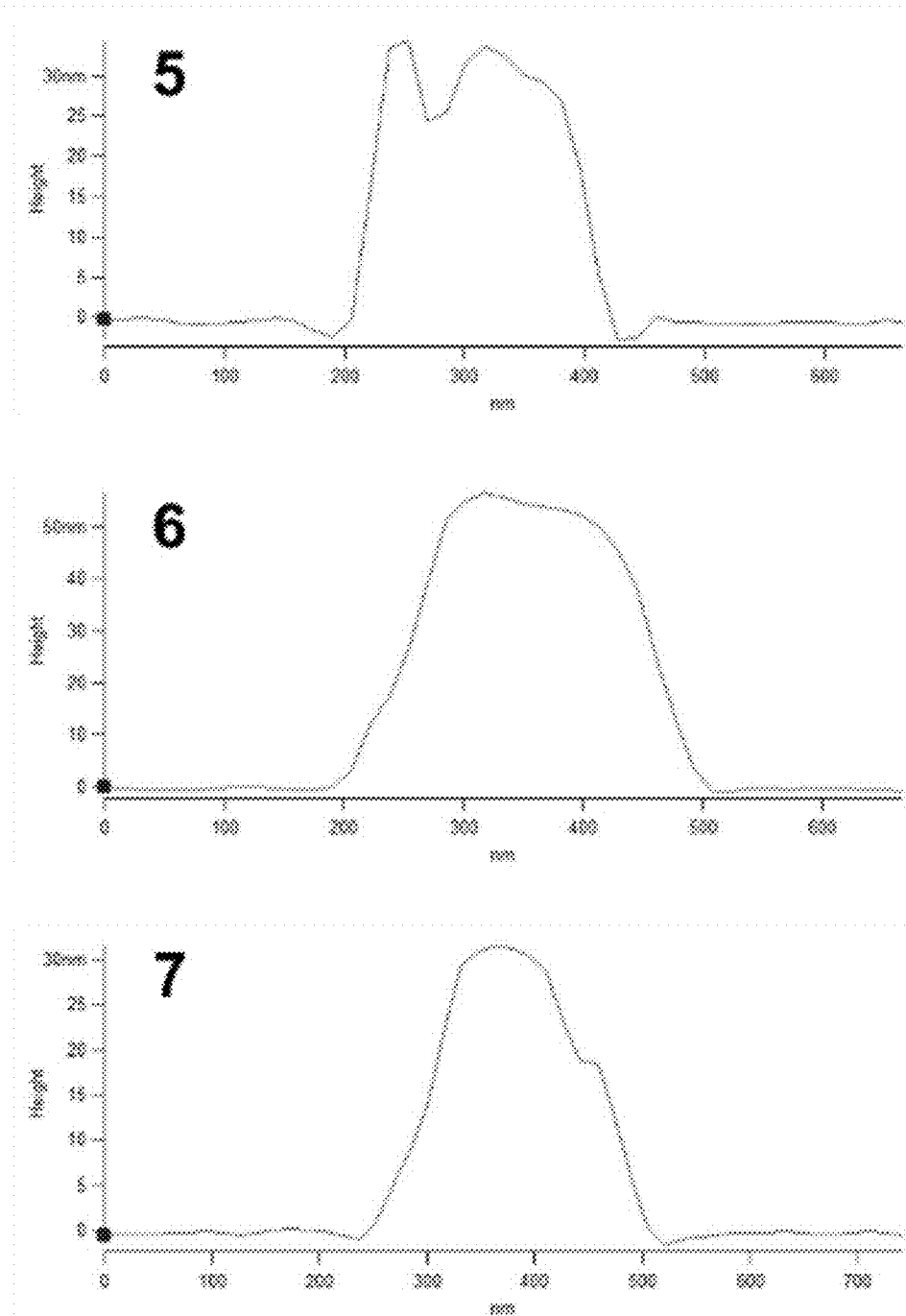
Figure 10:
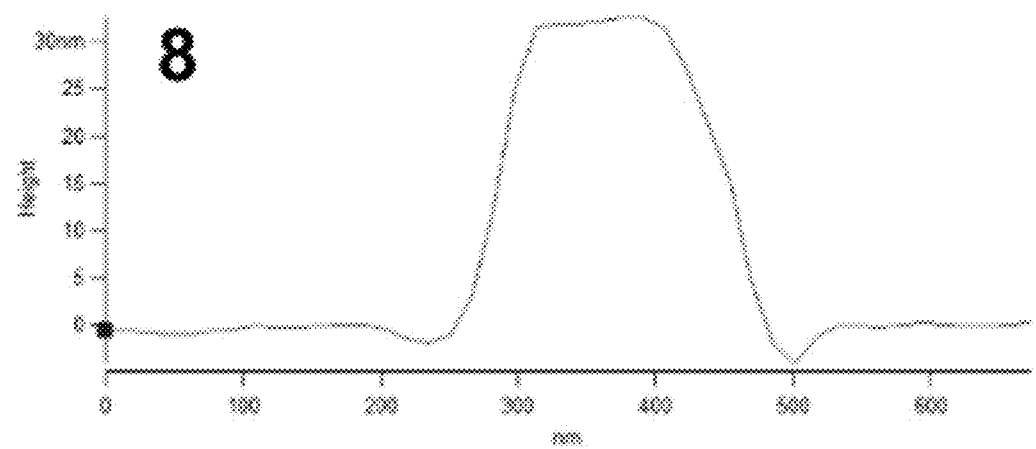
Figure 10:
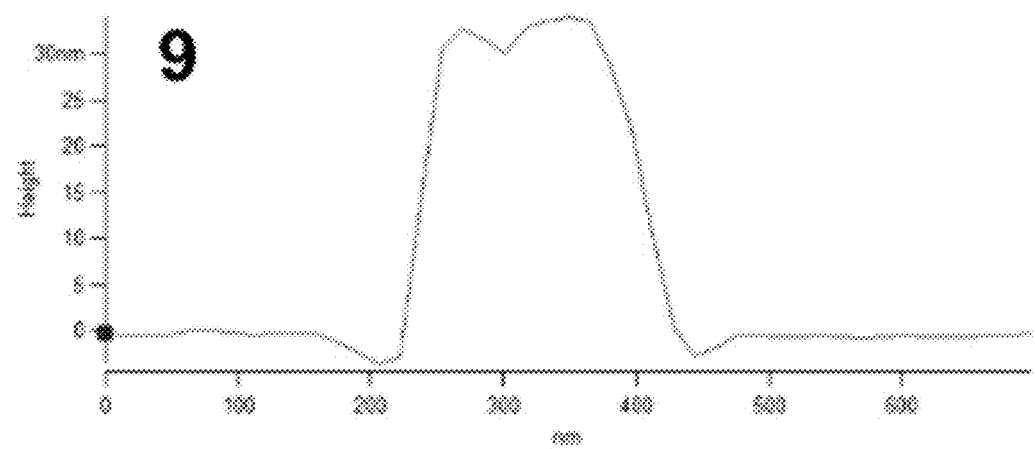
Figure 10:
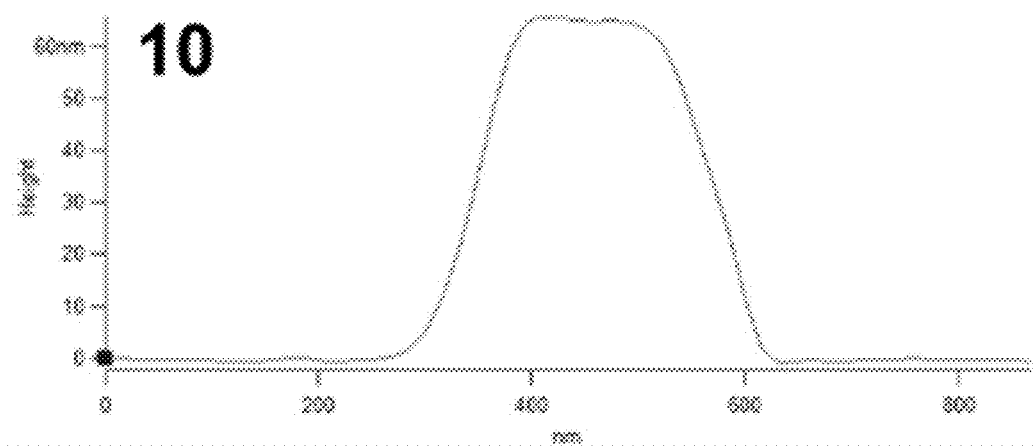
Figure 11:
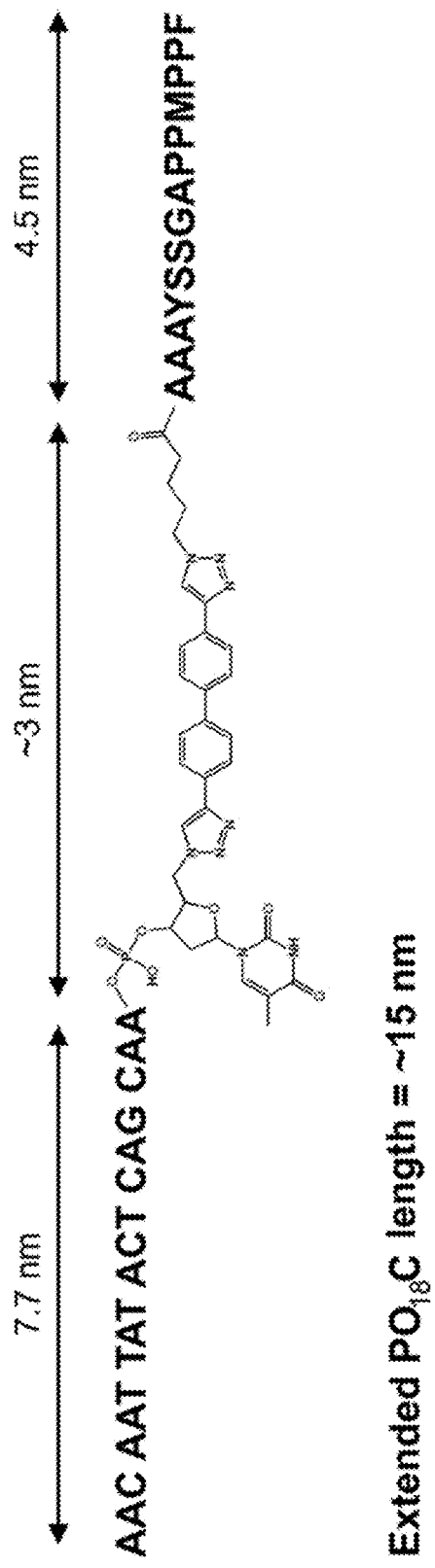
FIG. 11: $PO_{18}C$ length. The length of the extended 18mer oligonucleotide was reported to be 7.7 nm. See Wang, L., et al., Amphiphilic DNA-dendron hybrid: a new building block for functional assemblies. *Soft Matter* 2011, 7 (16), 7187-7190; Tinland, B., et al., Persistence Length of Single-Stranded DNA. Macromolecules 1997, 30 (19), 5763-5765. Figure discloses SEQ ID NOS 2 and 1, respectively, in order of appearance; SEQ ID NO: 2 is depicted in the figure in the 3' to 5' orientation and disclosed herein as 5'-AAC GAC TCA TAT TAA CAA-3'.
Figure 12:
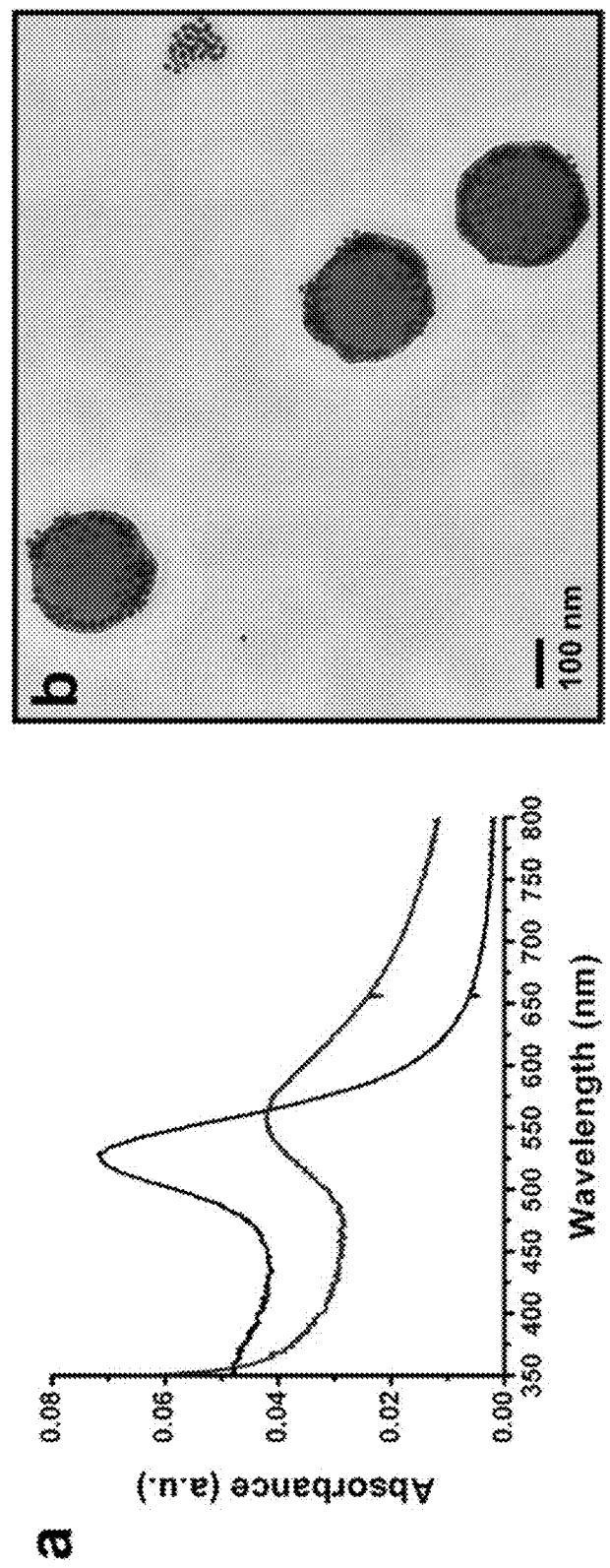
FIG. 12.
Figure 13:
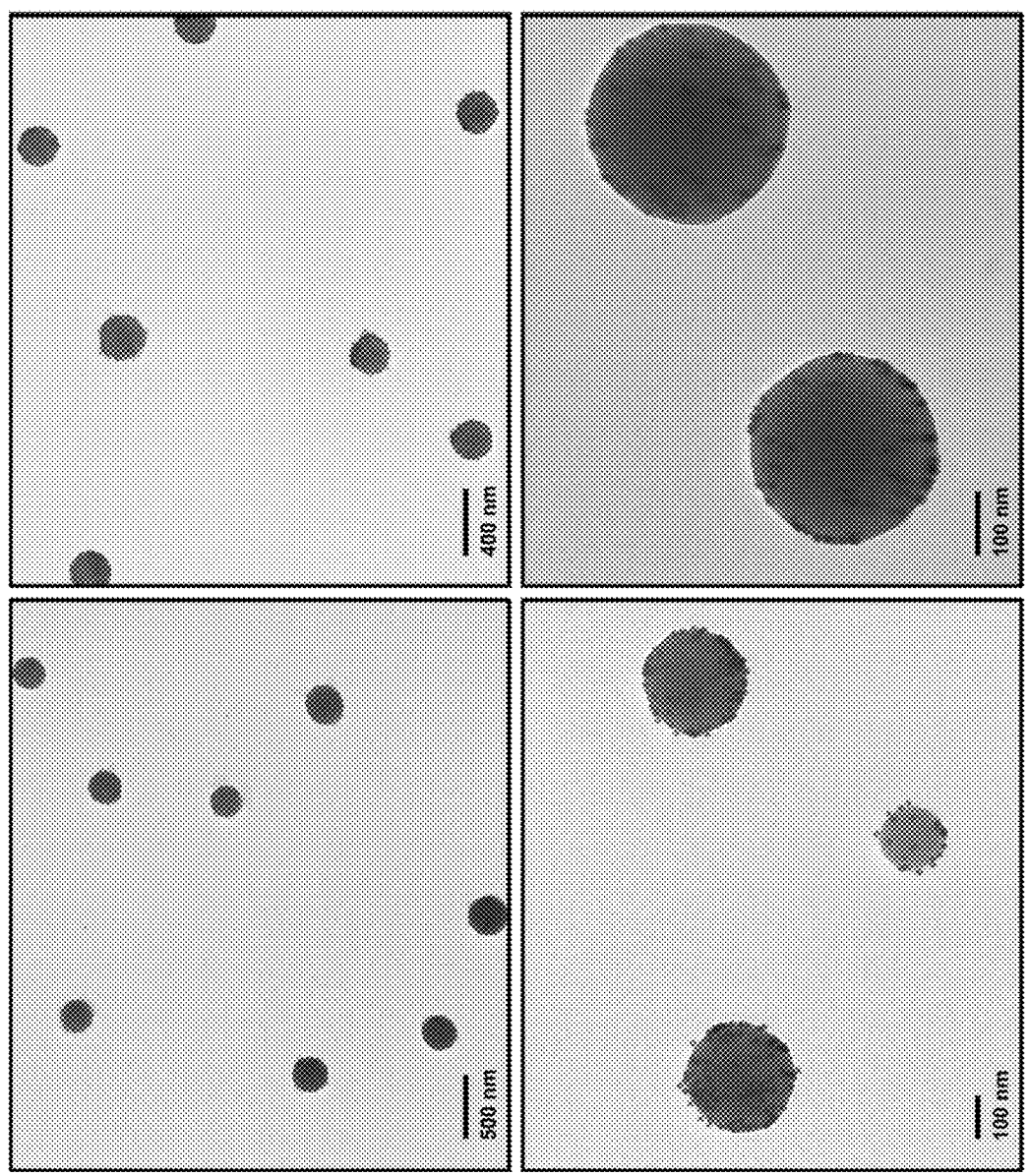
FIG. 13: Additional TEM images of gold nanoparticle-decorated $PO_{18}C$ vesicles after 2 hrs.
Figure 14:
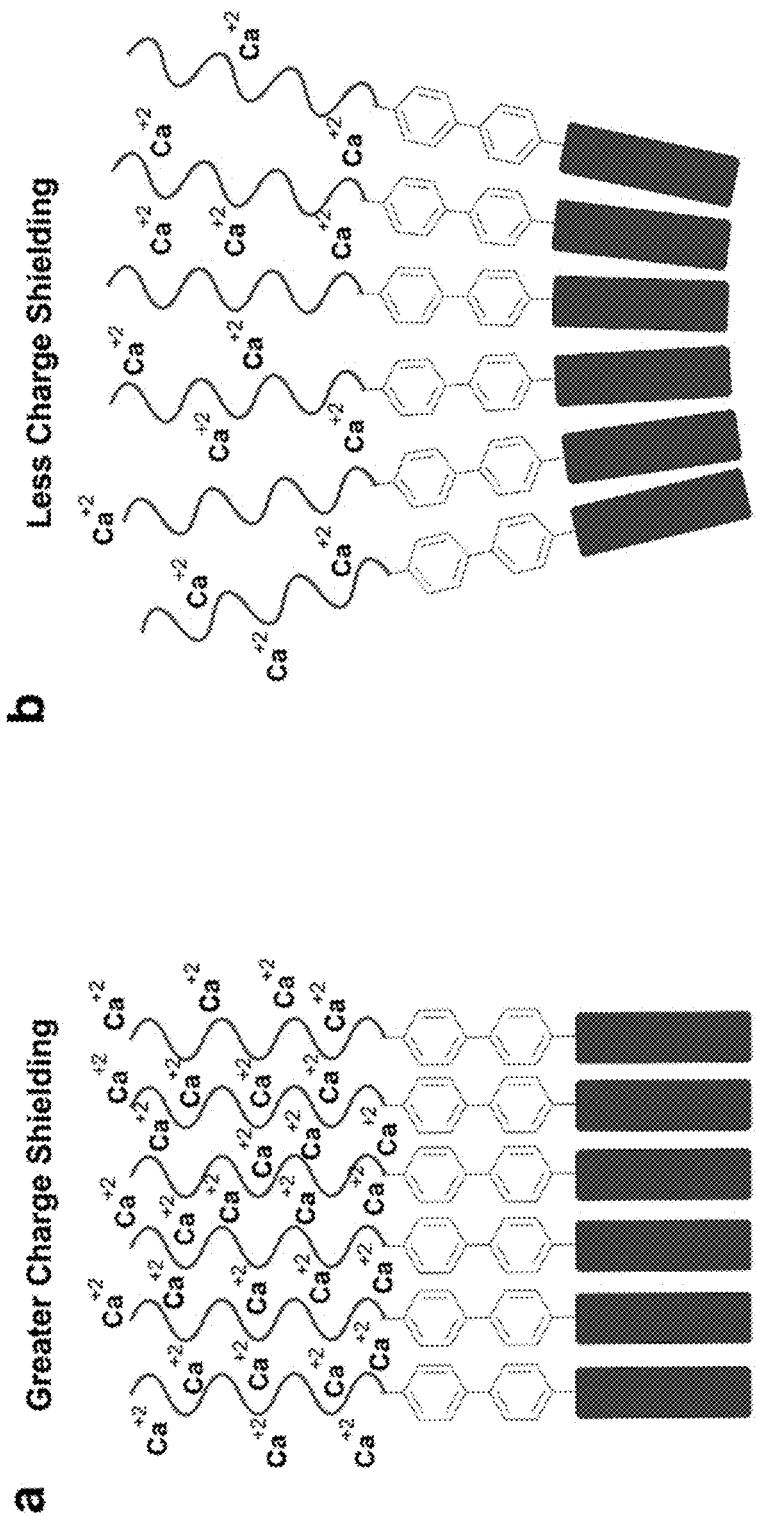
FIG. 14.
Figure 15:
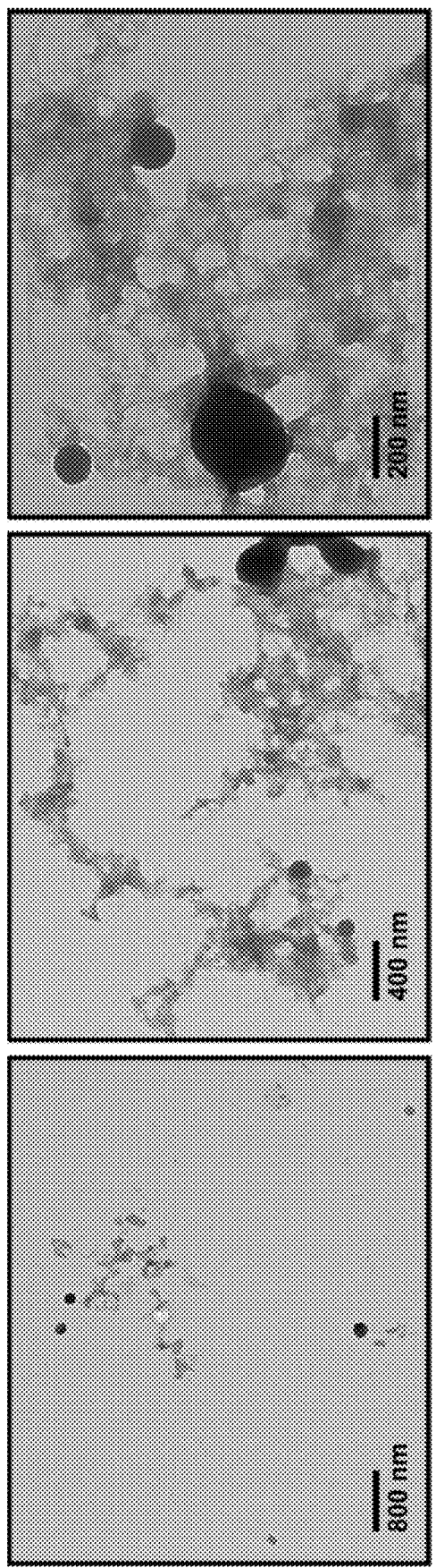
FIG. 15: TEM image of 500 μM $PO_6C$ in 10 mM $CaCl_2$) after 15-20 hrs. Fibers, aggregates, and spherical assemblies were observed.
Figure 16:
FIG. 16: TEM images of 500 μM $PO_6C$ in 50 mM $CaCl_2$) after 15-20 hrs. Fibers were observed.
Figure 17:
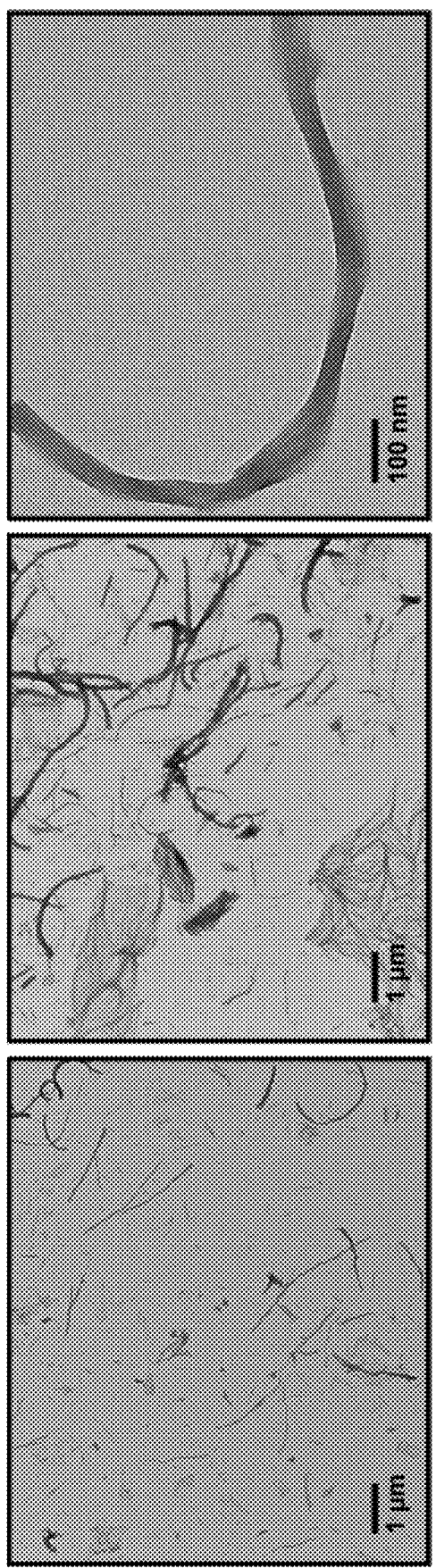
FIG. 17: TEM images of 500 μM $PO_6C$ in 150 mM $CaCl_2$) after 15-20 hrs. Fibers and fiber networks were observed.
Figure 18:
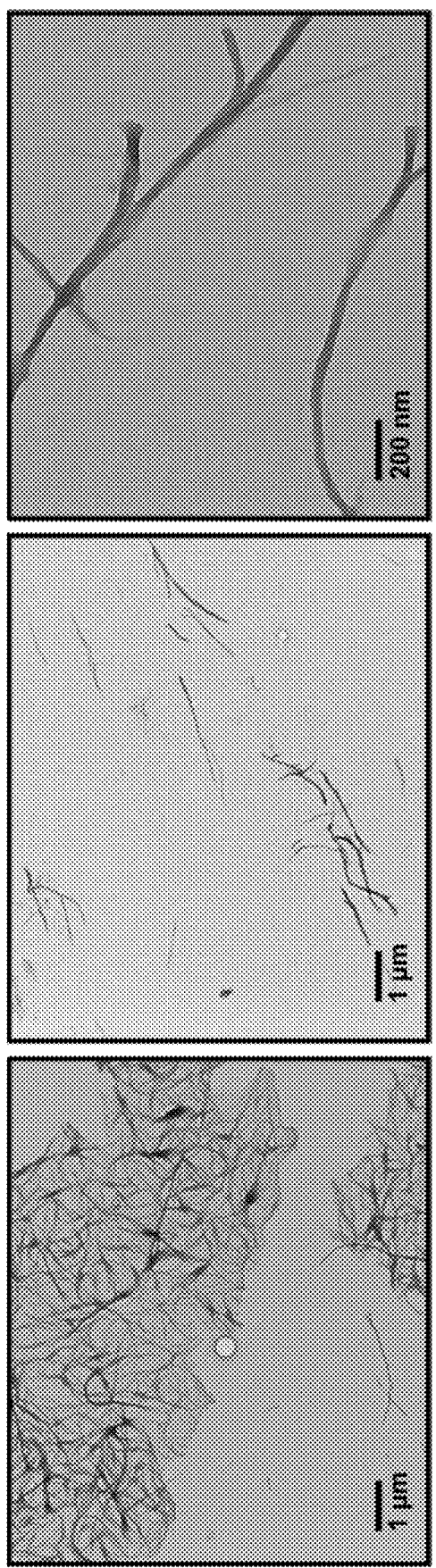
FIG. 18: TEM images of 500 μM $PO_6C$ in 300 mM $CaCl_2$) after 15-20 hrs. Fibers and fiber networks were observed.
Figure 19:
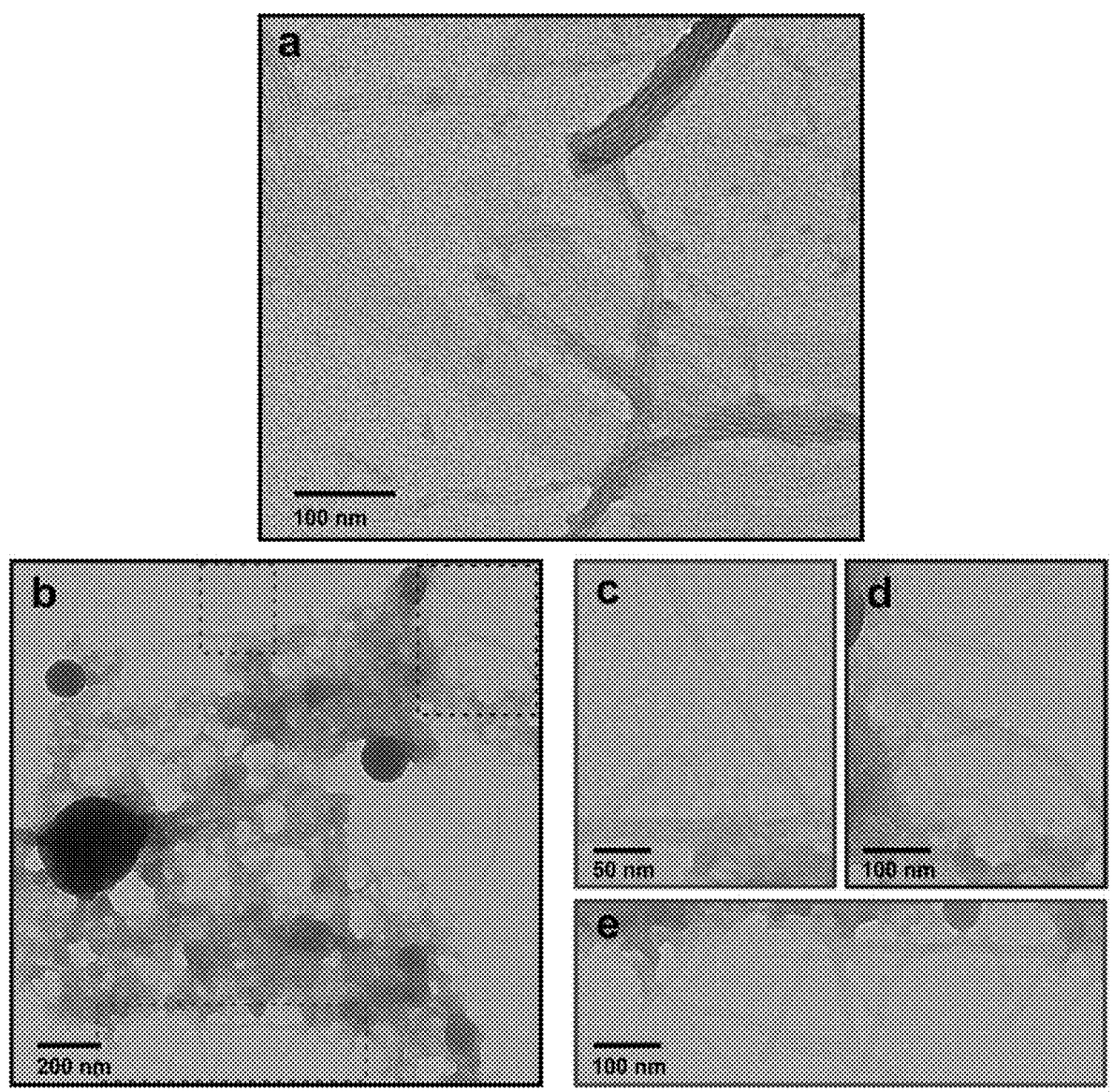
FIG. 19: $PO_6C$ assemblies assembled in (FIG. 19a) 50 mM $CaCl_2$) and (FIG. 19b) 10 mM $CaCl_2$).
Figure 20:
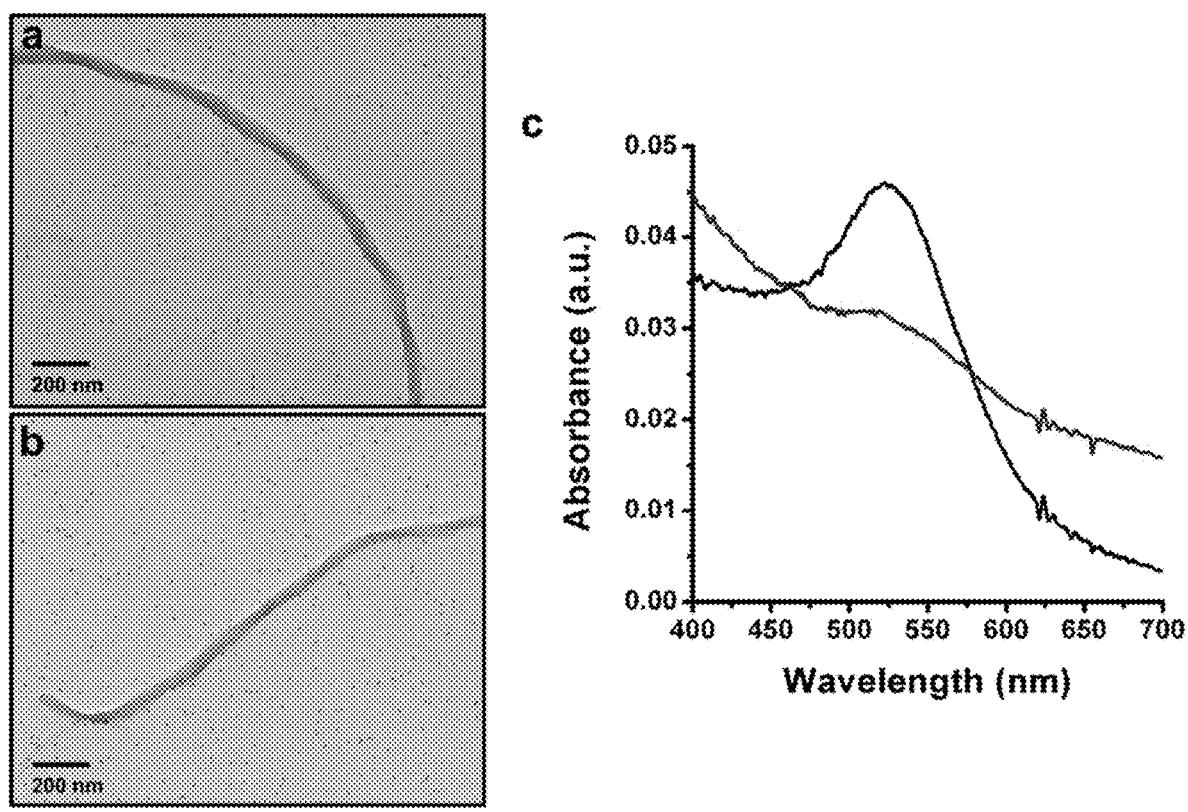
FIG. 20.
Figure 21:
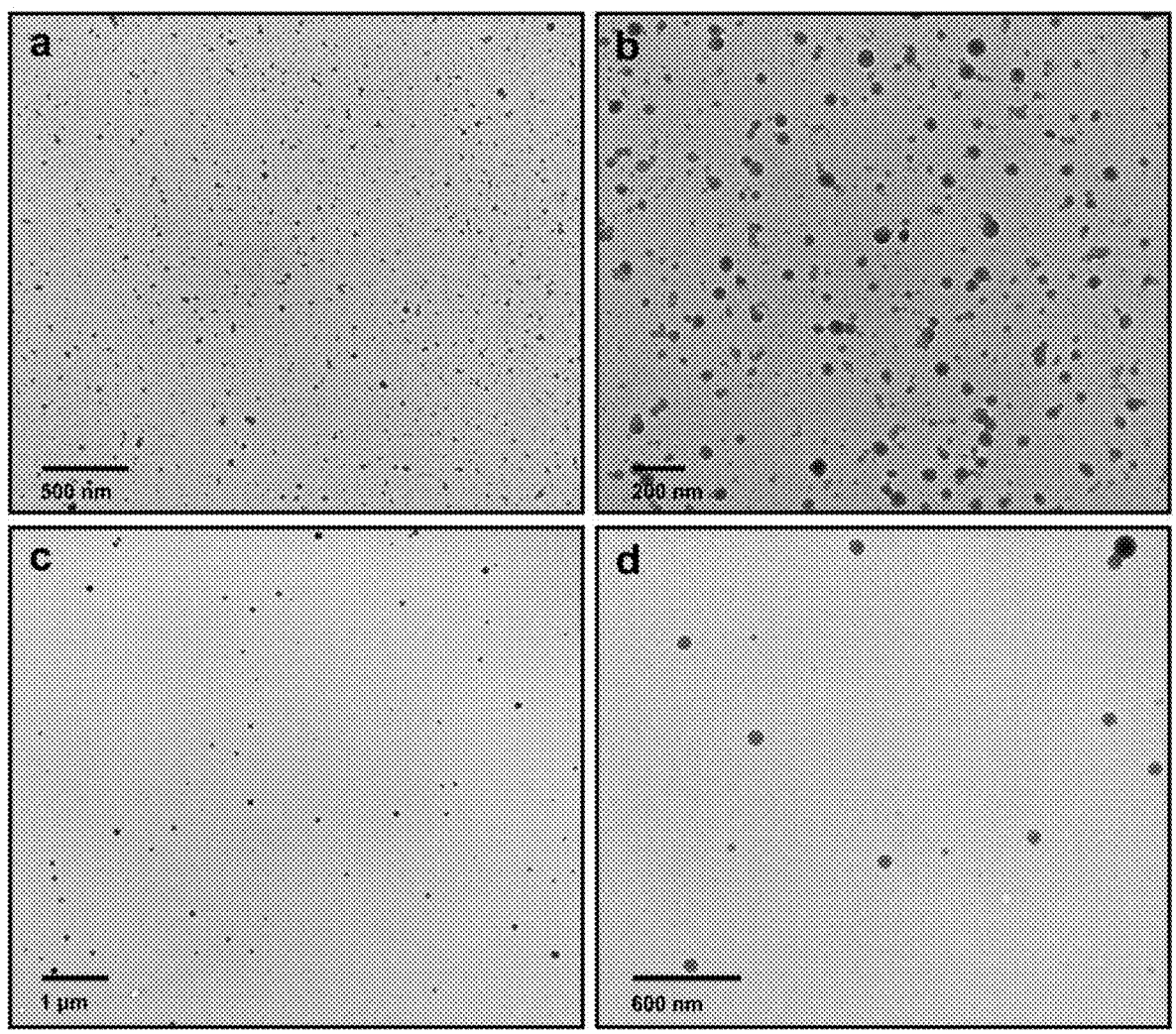
FIG. 21: $PO_{18}C$ (500 μM) assembled in the (FIG. 21a,b) absence of complement and in the (FIG. 21c,d) presence of complement. Both experiments were conducted in 150 mM $CaCl_2$).
Figure 22:
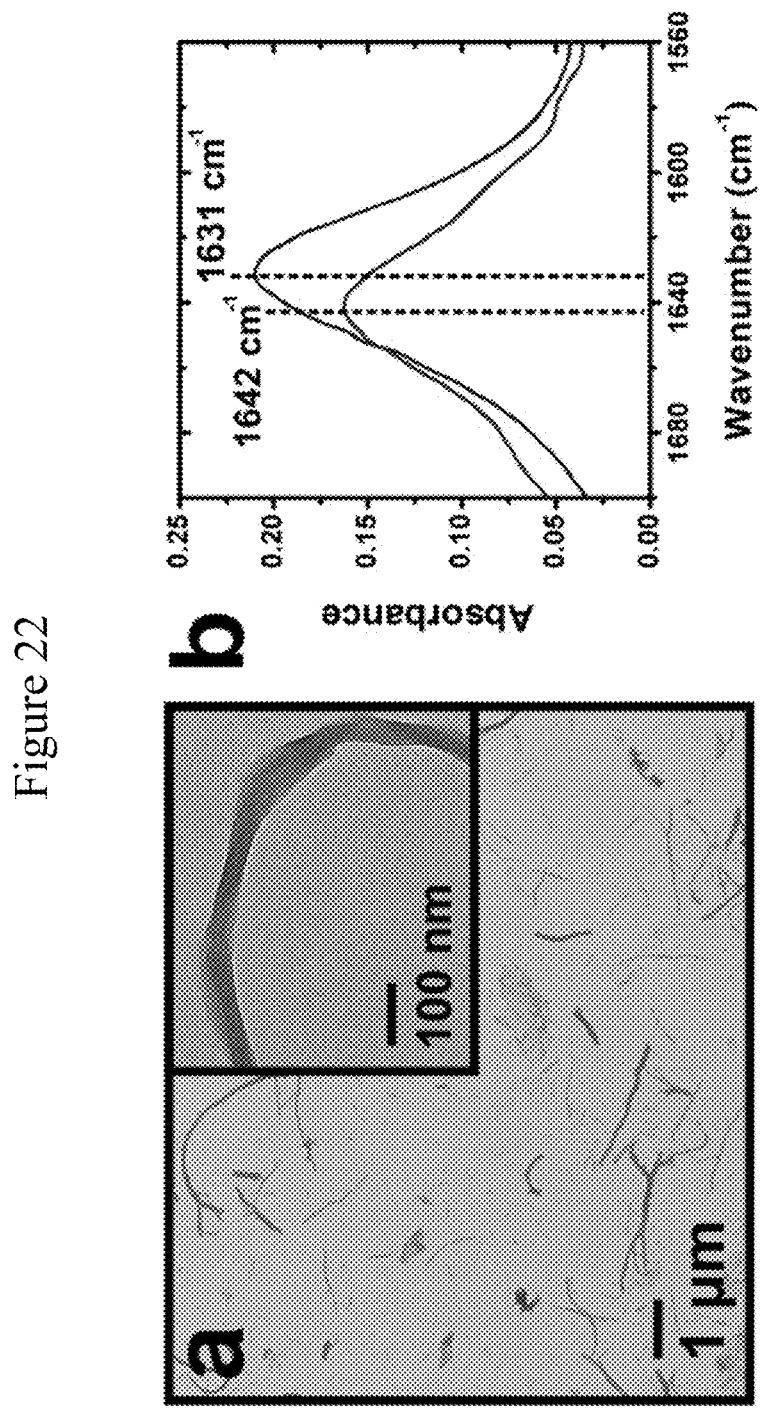
FIG. 22.

In some embodiments, the POC structure may be synthesized by coupling methods, such as copper (I) catalyzed "click" chemistry to covalently attach azido-modified peptides and oligonucleotides. For example, the Conjugation was achieved in a stepwise fashion: 1) the oligonucleotide, an azido-modified 18- or 6-base sequence (FIG. S1), was first attached to the biphenyl core using an established solid-phase synthesis method [Thaner et al., *Chem. Sci.*, 5: 1091-1096 (2014)]; and 2) the peptide, an N-terminal azido-modified peptide ($N_3$—$C_4H_8CO$-AAAYSSGAPPMPPF (SEQ ID NO: 1)), was next attached in the solution phase to yield the POCs (Scheme 1). Each $PO_nC$ (n=2-26) may be purified via reverse-phase high-performance liquid chromatography (HPLC), and their compositions can be confirmed by matrix-assisted laser desorption/ionization time-of-flight mass spectrometry (MALDI-TOF MS; FIG. 3).

4. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

As used herein, "about" will be understood by persons of ordinary skill in the art and will vary to some extent depending upon the context in which it is used. Certain ranges are presented herein with numerical values being preceded by the term "about". The term "about" is used herein to provide literal support for the exact number that it precedes, as well as a number that is near to or approximately the number that the term precedes. If there are uses of the term which are not clear to persons of ordinary skill in the art, given the context in which it is used, "about" will mean up to plus or minus 10% of the particular term, for example, ±1%, ±2%, ±3%, ±4%, ±5%, ±6%, ±7%, ±8%, ±9% or ±10%.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocycleoxy, and heterocyclealkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. As stated above, the present disclosure is understood to include embodiments where, for instance a "substituted alkyl" optionally contains one or more alkene and/or alkyne.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heteroaryl groups are aromatic ring compounds containing 5 or more ring members, of which, one or more is a heteroatom such as, but not limited to, N, O, S or B. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

As used herein, "natural amino acid" is defined to include amino acids identified in organisms living in a wild state and specifically including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

As used herein, "synthetic amino acid" is defined to include α-amino acids and β-amino acids that are not natural amino acids and include those known in the peptide chemistry arts for preparing synthetic analogs of naturally occurring peptides, including D and L forms.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

5. Examples (a) General Methods and Instrumentation:

All chemicals were purchased from either Aldrich or Fisher and used without further purification. $N_3$—$C_4H_8$CO-AAAYSSGAPPMPPF (SEQ ID NO: 1) ($N_3$-A2PEP$_{Au}$, Figure S2) was purchased from ThermoFisher Scientific. Gold nanoparticles were purchased from Ted Pella (#15702-20 and #15704-20 for 5 and 15 nm particles, respectively). Peptide oligonucleotide chimeras (POCs) were purified using an Agilent 1200 Series reverse-phase high-pressure liquid chromatography (HPLC) instrument equipped with an Agilent Zorbax 300SB-$C_{18}$ column. POCs were quantified based on their absorbance at 260 nm and using the total extinction coefficient of DNA (195,100 $M^{-1}cm^{-1}$ and 62,800 $M^{-1}cm^{-1}$ for $PO_{18}C$ and $PO_6C$, respectively). Spectra were collected using an Agilent 8453 UV-Vis spectrometer equipped with deuterium and tungsten lamps. Transmission electron microscopy (TEM) samples were prepared by drop-casting 4 μL of solution onto a 3-mm-diameter copper grid coated with formvar. After 4 min., the excess solution was wicked away and the grid was washed with nanopure $H_2O$ (4 μL) and wicked away immediately. TEM images were collected with a FEI Morgagni 268 (80 kV) equipped with an AMT side mount CCD camera system. AFM samples were prepared by drop-casting 6 μL of solution onto freshly cleaved mica or mica functionalized with 3-aminopropyltriethoxysilane(APTES) and air dried. The samples were washed with 30 μL nanopure $H_2O$ and wicked away (repeated once). The amples were allowed to air dry overnight. AFM images were collected with an Asylum WIFP-3D atomic force microscopy using tapping-mode. Images were obtained using ultra-sharp AFM tips (NanoandMore, SHR-150), with a 0.8 Hz scanning rate and 512 pixel resolution. Scanning electron microcopy (SEM) samples were prepared by drop-casting 5 μL of solution onto silicon wafers and allowed to air dry. The samples were then washed with 5 μL of nanopure H$_2$O (wicked immediately) and then allowed to air dry overnight. SEM images were collected using a ZEISS Sigma 500 VP SEM. Matrix-assisted laser desorption/ionization time-of-flight mass spectrometry (MALDI-TOF MS) data were collected using an Applied Biosystem Voyager System 6174 MALDI-TOF mass spectrometer (negative reflector mode; accelerating voltage: 20 kV) with 3-hydroxypicolinic acid (3-HPA) as the ionization matrix. Nanopure water (NP H$_2$O, 18.2 MΩ) was obtained from a Barnstead Diamond™ water purification system. All TEM measurements were made using ImageJ software.

(b) Preparation of Azido-Modified Oligonucleotide Conjugate ($O_{18}$—$N_3$ and $O_6$—$N_3$).

In a typical procedure, syntheses were carried out from the 3' direction using controlled pore glass (CPG) beads possessing 1 μmol of adenine (Glen Research, dA-CPG #20-2001-10, (1000 Å, 38 μmol/g)). The CPG beads were placed in a 1 μmol synthesis column and Ultramild 3'-phosphoramidites (Glen Research, Pac-dA-CE phosphoramidite #10-1601-05, Ac-dC-CE phosphoramidite #10-1015-05, iPr-Pac-dG-CE phosphoramidite #10-1621-05, dT-CE phosphoramidite #10-1030-05) and 5'-Iodo-dT phosphoramidite (Glen Research, #10-1931-90) were then added using the standard 1 μmol protocol on an Expedite 8909 synthesizer. Note, a mild Cap A Mix (Glen Research, 5% Phenoxyacetic anhydride in THF, #40-4212-52) was also used for synthesis due to the lability of the Iodo moiety. At the end of the synthesis, the beads were dried overnight and kept in a tightly capped vial at ambient conditions.

The terminal Iodo groups were substituted for azides using an established procedure. See Miller, G. P.; Kool, E. T., "Versatile 5'-Functionalization of Oligonucleotides on Solid Support: Amines, Azides, Thiols, and Thioethers via Phosphorus Chemistry," *The Journal of Organic Chemistry*, 69 (7): 2404-2410 (2004). The CPG beads were kept in the columns while a saturated mixture of sodium azide in anhydrous dimethylformamide (DMF) was prepared (approximately 30 mg per 1 mL, per 1 μmol). Upon pulling up 1 mL of the mixture in a syringe, the column was firmly attached with an empty syringe on one end and the one containing the mixture in the other. The mixture was slowly passed over the CPG beads several times before either being left at ambient overnight or placed in a shaker at 60° C. for one hour. The beads were then washed thoroughly with DMF and acetone before drying with nitrogen. The solid-phase coupling reactions with the organic core were performed using these dry CPG beads.

(c) Attachment of Azido-Modified Oligonucleotides to Diacetylene Biphenyl Organic Core Dry CPG beads containing azide-modified DNA were placed in an Eppendorf tube. The biphenyl core (200 mM in DMF, 200 equivalents based on the azide-DNA strands on CPG beads, assuming a 100% yield in the oligonucleotide synthesis), tris(3-hydroxypropyltriazolylmethyl) amine (THPTA, 100 mM in DMF, 100 equivalents based on the azide-DNA strands on CPGs), CuSO4.5H$_2$O (100 mM in DMF, 100 equivalents based on the azide-DNA strands on CPGs), and L-ascorbic acid (100 mM in DMF, 100 equivalents based on the azide-DNA strands on CPGs) were also added. The reaction mixture was then blanketed with nitrogen before capping and shook for 7 to 18 hours at 25° C. in an Eppendorf® Thermomixer® R (Eppendorf, #022670107) at 1000 rpm. It is important that the CPG beads are constantly agitated while mixing and not sitting at the bottom of the tube. Once the reaction was complete, the CPG beads were filtered using a one-side fritted 1 μmol Expedite DNA synthesis column (Glen Research, #20-0021-01), then the beads were washed with DMF (5×1 mL) and acetone (5×1 mL) and dried with nitrogen. The beads were then placed in 1 mL of AMA at 65° C. for 15 minutes to cleave the conjugates from the solid supports. Afterwards, the ammonia and methyl amine were removed by passing a stream of nitrogen over the solution. To the remaining material was added ultrapure deionized H$_2$O (affording roughly 1 mL at the end), and the resulting solution was filtered through 0.45 μm nylon syringe filter (Acrodisc® 13 mm syringe filter #PN 4426T). The filtered solution was purified using reverse-phase HPLC eluting with a linear gradient of CH3CN and 0.1 M TEAA (5/95 to 45/55 over 30 min.).

(d) Attachment of Azido-Modified Peptide onto the Biphenyl Organic Core.

The POCs were prepared using copper(I)-catalyzed azide-alkyne cycloaddition (CuAAC) 2 in which $N_3$-A2PEP$_{Au}$ (Figure S2) was reacted with the azido-modified 18mer and 6mer conjugates (Scheme S1). See Huisgen, R., 1.3-DIPOLARE CYCLOADDITIONEN—RUCKSCHAU UND AUSBLICK. Angewandte Chemie-International Edition, 75 (13): 604-637 (1963); Rostovtsev et al., "A Stepwise Huisgen Cycloaddition Process: Copper(I)-Catalyzed Regioselective 'Ligation' of Azides and Terminal Alkynes," *Angew. Chem. Int. Ed,* 41 (14): 2596-2599 (2002).

The following stock solutions were prepared: A, 198.3 mM CuSO4 in NP H$_2$O; B, 37.3 mM THPTA in NP H$_2$O; C, 2 M urea in NP H$_2$O; and D, 60.6 mM sodium ascorbate in NP H$_2$O. Lyophilized $N_3$-A2PEP$_{Au}$ (125 nmol) was dissolved in 70 μL of DMF and 50 μL of NP H$_2$O and the solution was transferred to a vial containing On-$N_3$ (100 nmol, Scheme 51). To this vial was added a mixture of A and B (1.05 μL A mixed with 5.58 μL B), 1.5 μL of C, and 13.8 μL of D. The vial was sealed with parafilm wrap, wrapped in aluminum foil, and stirred for at least 4 h at room temperature. DMF/NP H$_2$O (1:1) was added to bring the total volume to 500 μL. The resulting solution was desalted using a NAP-5 desalting column (GE Healthcare Life Sciences, #17-0853-02). The eluted solution was purified using reverse-phase HPLC eluting with a linear gradient of CH3CN and 0.1 M TEAA (5/95 to 45/55 over 30 min.).

(e) Assembly Experiments.

In a 250 μL plastic vial, lyophilized POCs (20 nmol) were dissolved in CaCl$_2$ solutions to yield the desired concentration. The solutions were sonicated for 2 min. and centrifuged briefly. The vials were placed in a 1.5 mL centrifuge tube containing water that was pre-heated at 80° C. in an Eppendorf® Thermomixer® R (Eppendorf, #022670107), and the POC solutions were allowed to incubate for 15 min. at 80° C. After incubation, the temperature setting was lowered 1° C. every 5 minutes until the temperature reached 25° C. At 70° C., the samples were centrifuged very briefly to maintain POC concentration of the solution. After cooling to 25° C., the POC solutions were removed from the 1.5 mL centrifuge tube and allowed to sit overnight at room temperature. TEM samples were prepared after 15 to 20 h.

(f) Preparation of Complementary DNA-Functionalized Gold Nanoparticles.

The 5 and 15 nm gold nanoparticles were functionalized using reported methods. See Hurst et al., "Maximizing DNA Loading on a Range of Gold Nanoparticle Sizes," Analytical Chemistry, 78 (24): 8313-8318 (2006). Lyophilized complementary oligonucleotides functionalized with a thiol hexyl linker at the 5' end (purchased from IDT, 10 OD) were dissolved in 200 μL of freshly prepared dithiothreitol (DTT) and phosphate buffer (PB) solution (100 mM DTT in 170 mM PB) to cleave any disulfide bonds. The solution was allowed to sit for 1 hr. The thiol-terminated oligonucleotides were separated from the DTT using a NAP-5 column. The purified oligonucleotides (in 1 mL NP $H_2O$) were then added to 10 mL of particles. The particle solution was allowed to sit overnight. The next morning, the concentrations of PB and sodium dodecyl sulfate (SDS) were brought to 0.01 M and 0.01%, respectively. The oligonucleotide/gold nanoparticle solution was allowed to incubate at room temperature for 30 min. The concentration of NaCl was increased slowly to 0.5 M (in 6 increments) using 2 M NaCl. After each addition of NaCl, the solution was sonicated for 10 sec. and incubated for 30 min. before the next addition. After the salting procedure, excess oligonucleotides were removed via centrifugation (1 hr.; 16,100×g for 15 nm particles and 10900×g for 5 nm particles), and subsequent supernatant removal. The remaining pellets were combined and the washing process was repeated twice. The final oligonucleotide/functionalized nanoparticle pellet was suspended in 100 µL of NP $H_2O$. The gold nanoparticle concentration was determined via UV-Vis spectroscopy using extinction coefficients of $2.4\times10^8$ L/(mol·cm)$^4$ and $9.696\times10^6$ L/(mol·cm) (from Ted Pella) for 15 and 5 nm particles, respectively. The concentrations of these stock solutions of nanoparticles were $4.09\times10^{14}$ and $2.17\times10^{13}$ particles in 100 µL NP $H_2O$ for the 5 nm and 15 nm stock solutions, respectively.

(g) Functionalized Gold Nanoparticle Addition to $PO_{18}C$ Vesicles.

To a solution of $PO_{18}C$ vesicles (30 µL) assembled in 50 mM $CaCl_2$ was added 1 µL of a 25× diluted solution of the 15 nm stock solution prepared above. The mixture was mixed and vortexed briefly and allowed to sit at room temperature. TEM samples were prepared after 1 hr.

(h) Functionalized Gold Nanoparticle Addition to $PO_6C$ Fibers.

To a solution of $PO_6C$ fibers (30 µL) assembled in 50 mM $CaCl_2$) was added 1 µL of a 10× diluted solution of the 5 nm stock solution prepared above. The mixture was mixed and vortexed briefly and allowed to sit at room temperature. TEM samples were prepared after 1 hr.

(i) Supplementary Information
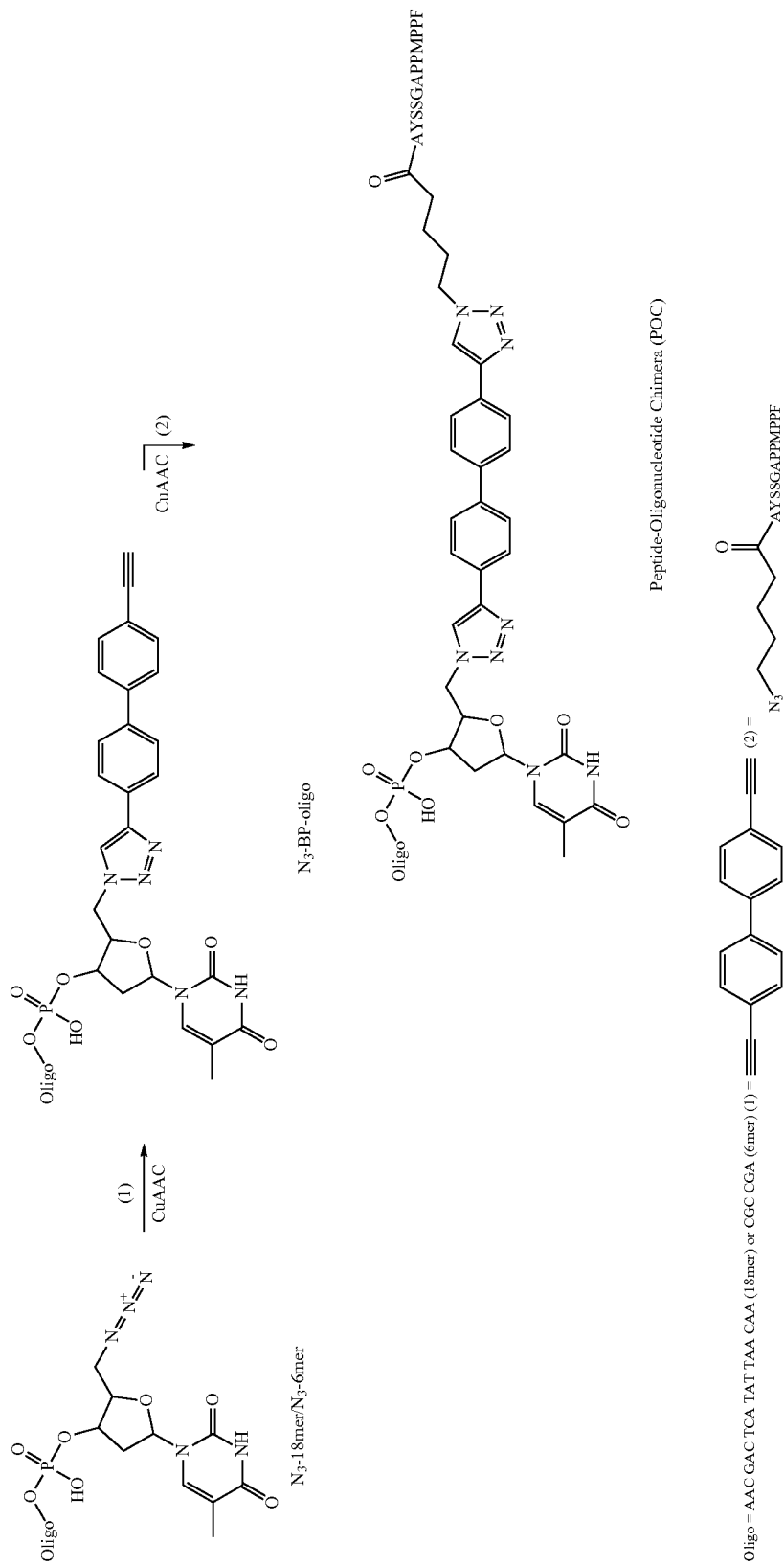

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound comprising a peptide segment and an oligonucleotide segment interlinked by an organic core moiety, wherein the compound is represented by the following formula (I):

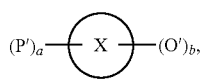

wherein P' is the peptide segment; O' is the oligonucleotide segment; X is the organic core moiety; a is 1-4 and b is 1-4, and wherein
the organic core moiety is comprised of an arylene moiety that is optionally substituted and/or a heteroarylene moiety that is optionally substituted.

2. The compound of claim 1, wherein the peptide segment comprises two or more natural or synthetic amino acids.

3. The compound of claim 2, wherein the peptide segment consists of natural or synthetic amino acids.

4. The compound of claim 1, wherein the peptide segment comprises about 2 to about 25 natural or synthetic amino acids.

5. The compound of claim 1, wherein the peptide segment comprises a peptide capable of forming β-sheets.

6. The compound of claim 1, wherein the peptide segment comprises a peptide capable of effecting an assembly to form self-assembling nanoscale systems.

7. The compound of claim 6, wherein the self-assembling nanoscale system is selected from the group consist of 1D fiber, a hollow sphere and a micelle-type structure.

8. The compound of claim 1, wherein the peptide segment comprises a therapeutic peptide.

9. The compound of claim 1, wherein the oligonucleotide segment comprises two or more modified or unmodified nucleosides comprising natural or synthetic nucleobases and modified or unmodified internucleoside linkages.

10. The compound of claim 1, wherein the oligonucleotide segment comprises an antisense oligonucleotide.

11. The compound of claim 1, wherein the organic core moiety comprises an aliphatic moiety that is optionally substituted.

12. The compound of claim 1, wherein a and b are each 1.

13. The compound of claim 1, wherein a is 1 and b is 2, 3, or 4.

14. The compound of claim 1 of formula:

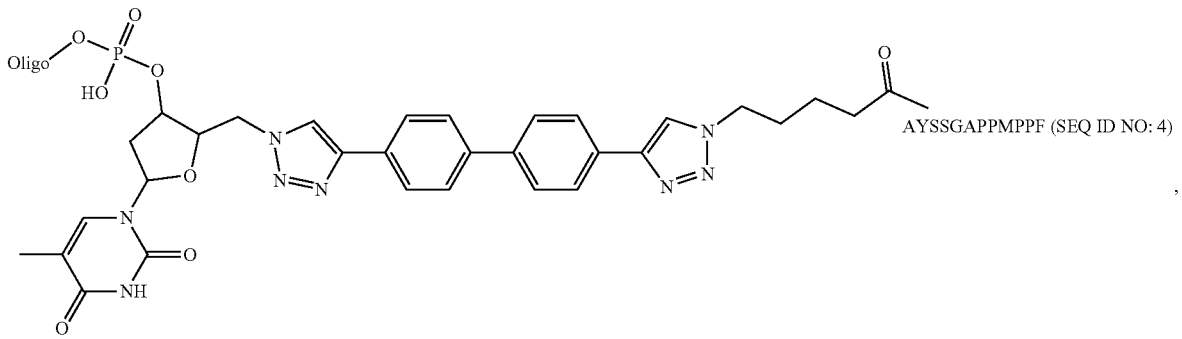

wherein oligo comprises an oligonucleotide.

15. The compound of claim 14, wherein the oligonucleotide comprises AAC GAC TCA TAT TAA CAA- (SEQ ID NO: 2) or CGC CGA-.

16. The compound of claim 1 of formula:

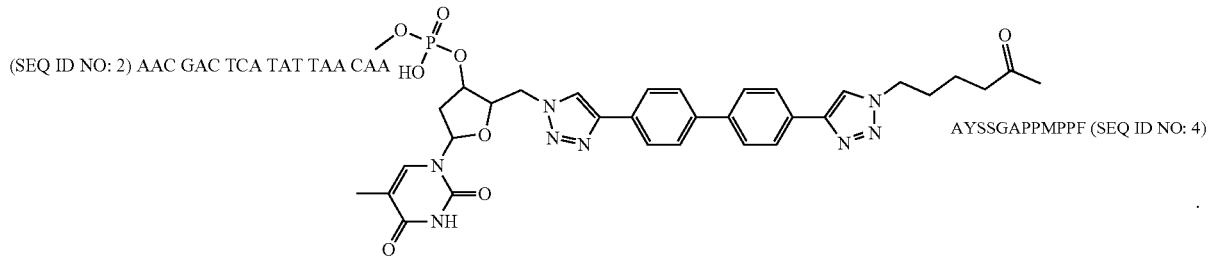 [SMILES: COP(=O)(O)OC1CC(n2cc(C)c(=O)[nH]c2=O)OC1Cn1cc(-c2ccc(-c3ccc(-c4cn(CCCCC(C)=O)nn4)cc3)cc2)nn1]

17. A nanostructure composition comprising a plurality of compounds according to claim 1.

18. The nanostructure composition of claim 17, wherein the nanostructure is a 1D fiber.

19. The nanostructure composition of claim 17, wherein the nanostructure is a hollow sphere.

20. The nanostructure composition of claim 19, wherein the hollow sphere comprises a monolayer of the plurality of compounds with the oligonucleotide segments directed towards the outer surface.

21. The nanostructure composition of claim 19, wherein the hollow sphere has a diameter of about 10 to about 500 nm.

\* \* \* \* \*

UNITED STATES PATENT AND TRADEMARK OFFICE
CERTIFICATE OF CORRECTION

PATENT NO. : 11,491,231 B2
APPLICATION NO. : 15/941626
DATED : November 8, 2022
INVENTOR(S) : Rosi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 802 days.

Signed and Sealed this
Fourteenth Day of January, 2025

Derrick Brent
*Acting Director of the United States Patent and Trademark Office*